United States Patent
Florez et al.

(10) Patent No.: US 11,857,651 B2
(45) Date of Patent: Jan. 2, 2024

(54) COMPOSITIONS WITH DOPED TITANIUM DIOXIDE NANOPARTICLES AND METHODS OF USE

(71) Applicant: The Board of Regents of the University of Oklahoma, Norman, OK (US)

(72) Inventors: Fernando Luis Esteban Florez, Moore, OK (US); Sharukh Soli Khajotia, Edmond, OK (US); Adam Justin Rondinone, Knoxville, TN (US)

(73) Assignees: The Board of Regents of the University of Oklahoma, Norman, OK (US); UT-Battelle, LLC, Oak Ridge, TN (US)

( * ) Notice: Subject to any disclaimer, the term of this patent is extended or adjusted under 35 U.S.C. 154(b) by 1148 days.

(21) Appl. No.: 16/467,387

(22) PCT Filed: Dec. 7, 2017

(86) PCT No.: PCT/US2017/065103
§ 371 (c)(1),
(2) Date: Jun. 6, 2019

(87) PCT Pub. No.: WO2018/106912
PCT Pub. Date: Jun. 14, 2018

(65) Prior Publication Data
US 2020/0085698 A1 Mar. 19, 2020

Related U.S. Application Data

(60) Provisional application No. 62/431,604, filed on Dec. 8, 2016.

(51) Int. Cl.
| | |
|---|---|
| A61K 6/844 | (2020.01) |
| A61C 5/30 | (2017.01) |
| A61K 6/816 | (2020.01) |
| A61K 6/69 | (2020.01) |
| A61K 6/62 | (2020.01) |
| A61K 6/17 | (2020.01) |
| A61C 19/06 | (2006.01) |

(52) U.S. Cl.
CPC .............. *A61K 6/844* (2020.01); *A61C 5/30* (2017.02); *A61C 19/063* (2013.01); *A61K 6/17* (2020.01);
(Continued)

(58) Field of Classification Search
CPC ...................................................... A61K 6/844
See application file for complete search history.

(56) References Cited

U.S. PATENT DOCUMENTS

| | | |
|---|---|---|
| 6,071,528 A | 6/2000 | Jensen |
| 6,984,261 B2 | 1/2006 | Cummings et al. |

(Continued)

FOREIGN PATENT DOCUMENTS

| | | |
|---|---|---|
| EP | 2603159 A1 | 6/2013 |
| JP | 2003012431 A | 1/2003 |

(Continued)

OTHER PUBLICATIONS

Huo, Y., et al.; "Highly Active TiO2-xNx Visible Photocatalyst Prepared by N-Doping in Et3N/EtOH Fluid under Supercritical Conditions"; J. Phys. Chem. 112 (2008) 6546-6550.

(Continued)

*Primary Examiner* — Benjamin J Packard
(74) *Attorney, Agent, or Firm* — Hall Estill Law Firm

(57) ABSTRACT

A dental composition comprising doped TlO2 nanoparticles, and a curable resin material, wherein the curable resin material comprises a polymer precursor component, and wherein the dopant may be one or more of, for example, N (nitrogen), Ag (silver), F (fluorine), P (phosphorus), and PO4 (phosphate). A method of using the dental composition in a dental application. The dental composition may be antibacterial in the absence of visible light or UV light.

20 Claims, 15 Drawing Sheets

(52) U.S. Cl.
CPC .................. *A61K 6/62* (2020.01); *A61K 6/69* (2020.01); *A61K 6/816* (2020.01)

(56) References Cited

U.S. PATENT DOCUMENTS

| | | |
|---|---|---|
| 7,022,173 B2 | 4/2006 | Cummings et al. |
| 7,090,721 B2 | 8/2006 | Craig et al. |
| 7,250,155 B2 | 7/2007 | Yamaguchi et al. |
| 7,501,457 B2 | 3/2009 | Angermann et al. |
| 7,601,457 B2 | 3/2009 | Angermann et al. |
| 7,691,919 B2 | 4/2010 | Smolak et al. |
| 7,713,955 B2 | 5/2010 | Whiteford et al. |
| 7,963,769 B2 | 6/2011 | Qian |
| 7,968,618 B2 | 6/2011 | Chen et al. |
| 8,067,402 B2 | 11/2011 | Whiteford et al. |
| 8,067,403 B2 | 11/2011 | Whiteford et al. |
| 8,604,115 B1 | 12/2013 | Al-Harthi et al. |
| 9,212,286 B2 | 12/2015 | Whiteford et al. |
| 9,452,112 B2 | 9/2016 | Lu |
| 2006/0210798 A1 | 9/2006 | Burda |
| 2007/0178220 A1 | 8/2007 | Karlinsey |
| 2008/0187457 A1 | 8/2008 | Mangiardi |
| 2009/0023856 A1 | 1/2009 | Nakatsuka et al. |
| 2010/0291166 A1 | 11/2010 | Guyot-Ferreol et al. |
| 2011/0124492 A1 | 5/2011 | Loukine et al. |
| 2011/0266136 A1 | 11/2011 | Varma et al. |
| 2011/0275035 A1 | 11/2011 | Lu |
| 2012/0172485 A1 | 7/2012 | Sun et al. |
| 2013/0023601 A1 | 1/2013 | Ogliari et al. |
| 2015/0190313 A1 | 7/2015 | Inaki et al. |
| 2016/0058675 A1 | 3/2016 | Xu et al. |
| 2016/0228335 A1 | 8/2016 | Xu et al. |

FOREIGN PATENT DOCUMENTS

| | | |
|---|---|---|
| JP | 2008023003 A | 2/2008 |
| KR | 20160077994 A | 7/2016 |
| WO | 2007016508 A1 | 2/2007 |

OTHER PUBLICATIONS

Dinh, C-T, et al.; "Shape-Controlled Synthesis of Highly Crystalline Titania Nanocrystals"; ACS Nano 3:11 (2009) 3737-3743.

Sun, J., et al.; "Improving performance of dental resins by adding titanium dioxide nanoparticles"; Dental Materials (2011) 11 pages.

Brock, J., et al.; "Antibacterial and wetting behavior of doped titanium dioxide nanoparticles in dental adhesive resin"; Dept. of Dental Materials, College of Dentistry, University of Oklahoma Health Sciences Center (2013) 1 page.

Asahi, R., et al.; "Nitrogen-Doped Titanium Dioxide as Visible-Light-Sensitive Photocatalyst: Designs, Developments, and Prospects"; Chem. Rev. 114 (2014) 9824-9852.

Chan, T., et al.; "Wettability of a novel dental adhesive resin containing doped titanium dioxide nanoparticles"; Dept. of Dental Materials, University of Oklahoma Health Sciences Center (2014) 1 page.

Florez, F., et al.; "Adhesive-resins Modified by Nitrogen-doped TiO2 Nanoparticles: Antibacterial and Wettability Behavior"; University of Oklahoma Health Sciences Center (2014) 1 page.

Florez, F.L.E., et al.; "Antibacterial and wetting behavior of experimental dental adhesive resins"; Dept. of Dental Materials, University of Oklahoma Health Sciences Center (2014) 1 page.

Benton, M, et al.; "Wettability and antibacterial efficacy of dental adhesive containing doped TIO2 Nanoparticles"; Dept. of Dental Materials, University of Oklahoma Health Sciences Center (2015) 1 page.

Florez, F.L.E., et al.; "Antibacterial and Wettability Characteristis of Dental Adhesives Containing Doped-TiO2 Nanoparticles"; College of Dentistry, University of Oklahoma Health Sciences Center (2015) 1 page.

Florez, F.E., et al.; "Surface Characterization of a Novel Antibacterial Dental Adhesive Resin"; IADR Abstract Archives (2015) 2 pages.

Bakar, S.A., et al.; "Nitrogen-doped titanium dioxide: An overview of material design and dimensionality effect over modern applications"; Journal of Photochemistry and Photobiology C: Photochemistry Reviews 27 (2016) 1-29.

Vu, D., et al.; "Wettability, color stability and fracture toughness of adhesives containing metal oxide nanoparticles"; Dept. of Dental Materials, University of Oklahoma Health Sciences Center (2016) 1 page.

Zane, A., et al.; "Biocompactibility and antibacterial activity of nitrogen-doped titanium dioxide nanoparticles for use in dental resin formulations"; International Journal of Nanomedicine 11 (2016) 6459-6470.

PCT/US2017/065103; "International Search Report and Written Opinion"; dated Feb. 9, 2018; 15 pages.

COMPOSITIONS WITH DOPED TITANIUM DIOXIDE NANOPARTICLES AND METHODS OF USE

CROSS REFERENCE TO RELATED APPLICATIONS

The present application is a national stage application of a PCT application having International Application No. PCT/US2017/065103, filed Dec. 7, 2017, which claims priority to U.S. Provisional Application having U.S. Ser. No. 62/431,604, filed Dec. 8, 2016, which claims the benefit under 35 U.S.C. 119(e), the disclosure of which is hereby expressly incorporated herein by reference.

GOVERNMENT SUPPORT

This invention was made with government support under Grant Numbers CNMS2013-331 and CNMS2015-331 granted by the U.S. Department of Energy, Office of Science, Oak Ridge National Laboratory. The government has certain rights in the invention.

BACKGROUND

Diseases related to pathogenic microorganisms (Gram-positive and Gram-negative bacteria, viruses and fungi) kill more people worldwide than any other single cause. These diseases are particularly important in the fields of medicine, dentistry, pharmaceuticals, cosmetics and water treatment. In dentistry, it is well documented that majority of oral diseases are related to the establishment of biofilms. Oral biofilms attach to natural and synthetic surfaces (abiotic and biotic) in the oral cavity. The formation of cariogenic (caries-producing) biofilms at the interface between a bonded resin restoration and tooth structure leads to the occurrence of secondary or recurrent caries. In fact, secondary caries at the restoration margins has been previously demonstrated to be one of the primary causes of failure of dental restorations. The replacement of failed restorations accounts for around 60% of all restorations performed in the USA each year at an annual cost of over $5 billion. Gingival margins of restorations are more prone to failure by secondary caries, because they are susceptible to contamination by oral fluids during the restorative procedures, lack of adaptation of the restorative material at the gingival margin, polymerization shrinkage and difficulty with effective control of biofilm (plaque) formation and accumulation at interproximal or sub-gingival areas.

The problem is exacerbated further because resin restorations have shorter service lives, tend to accumulate more biofilms when compared to enamel and other restorative materials, and the biomass accumulated on these particular surfaces is more cariogenic in nature. Studies regarding the effects of extractable components of resin composites over the growth of oral microorganisms have demonstrated that some leachable co-monomers, such as EDMA and TEGDMA, upregulate the growth of acidogenic microorganisms, which adversely degrade the materials' surface and the interfacial layer, and irritate the tooth's pulpal tissue. Most importantly, it could result in the artificial selection of biomasses with higher cariogenic potential, which predisposes to major shifts in the ecology of oral biofilms and triggers the development of oral diseases such as caries and periodontitis. In this context, it is of critical importance that antibacterial restorative dental biomaterials be developed to combat these issues. Ideally, these materials should have (i) superior levels of biocompatibility, (ii) must serve as scaffolds for the deposition of a hydroxyapatite-like layer that will reinforce the tooth structure and promote the attainment of a less porous adhesive layer, (iii) be acid resistant, and should have (iv) self-healing (v) self-cleaning and (vi) antibacterial capabilities.

As a consequence, several research groups have focused their efforts on the improvement of the biological and antibacterial behaviors of resin composites and the associated adhesive resins. Previous studies have investigated the effects of the incorporation of some antibacterial agents such as fluoride ($F^-$), chlorhexidine, nanohydroxyapatite, nanofluorohydroxyapatite, calcium fluoride ($CaF_2$), calcium phosphate (CaP), quaternary ammonium dimethacrylate (QADM), dimethylaminododecyl methacrylate (DMADDM), 12-methacryloyloxydodecylpyridinium bromide (MDPB), silver nanoparticles (nAg), zinc oxide (ZnO) and titanium dioxide nanoparticles ($TiO_2$ NPs) on the antibacterial properties of resin-based restorative materials against several oral microorganisms such as *Streptococcus mutans, Streptococcus mitis, Prevotella intermedia* and *Porphyromonas gingivalis*.

Photochemical sterilization of *Lactobacillus acidophilus, Saccharomyces cerevisiae* and *Escherichia coli* using titanium dioxide ($TiO_2$ or titania) powders and halide lamp irradiation for 60-120 min has been shown. Further, the photocatalytic action of titania has been shown to inactivate several microorganisms including Gram-positive and Gram-negative bacteria, fungi, algae and viruses. $TiO_2$ is an n-type semiconductor that has three crystalline polymorphs: anatase, brookite, and rutile with band gaps of 3.2 eV, 3.1 eV and 3.0 eV, respectively. The fundamental mechanism of $TiO_2$ photocatalysis is based on the interaction of light of appropriate wavelength and with adequate photonenergy with the surface of the photocatalyst. If this fundamental electronic requirement is satisfied (i.e., anatase polymorph requires 385 nm and at least 3.2204 eV), electrons pertaining to the valence band (fundamental energy state) will be promoted into the conduction band (higher energy state) leaving a positively charged electron vacancy (also known as hole) in the valence band. The resultant free electrons located at the conduction band ($e^-_{CB}$) and the positively charged holes ($h^+_{VB}$) at the valence band display strong reducing and oxidizing behaviors (Equation 1).

At this point, newly generated electrons ($e^-_{CB}$) and holes ($h^+_{VB}$) may recombine to release the excess of energy in the format of heat or light. If recombination doesn't occur and the newly generated $e^-_{CB}$ and $h^+_{VB}$ migrate to the photocatalyst's surface, then they can participate in numerous oxidation and reduction reactions with organic molecules. These reactions will generate some reactive oxygen species (ROS), as described in the Equations 2 and 3. Follow-on reactions (Equations 4-7) can generate hydrogen peroxide ($H_2O_2$) or hydroperoxyl radicals (•OOH)

$$TiO_2 + h\nu \rightarrow e^-_{CB} + h^+_{VB} \tag{1}$$

$$H_2O + h^+_{VB} \rightarrow \cdot OH + H^+ \tag{2}$$

$$OH^- + h^+_{VB} \rightarrow \cdot OH \tag{3}$$

$$2O\cdot_2^- + 2H^+ \rightarrow H_2O_2O_2 \tag{4}$$

$$\cdot OH + \cdot OH \rightarrow H_2O_2 \tag{5}$$

$$O\cdot_2^- + H_2O_2 \rightarrow \cdot OH + OH^- + O_2 \tag{6}$$

$$O\cdot_2^- + H^+ \rightarrow \cdot OOH \tag{7}$$

Although the use of photocatalysis to inactivate microorganisms has been comprehensively demonstrated over the past four decades, the complete antibacterial mechanism underlying the $TiO_2$ photocatalysis remains to be fully elucidated. It is believed that free radicals generated upon the irradiation of the $TiO_2$ photocatalyst attack preferentially polyunsaturated phospholipids localized at the microorganisms' membrane causing denaturation of proteins, electron mediators, membrane disruption and cytoplasm leakage, which consequently leads to the subsequent inactivation and death of cells.

Even though the photocatalytic process involving $TiO_2$ is a feasible technology, its efficacy is dependent on the use of UV irradiation at levels extremely dangerous to human cells and tissues, which significantly restricts the application of such technology in the oral cavity. Nevertheless, the successful incorporation of up to at least 30% of $TiO_2$ NPs into dental adhesive resins has been demonstrated. Experimental adhesive resins containing $TiO_2$ NPs have been shown to have antibacterial and bioactive properties when irradiated with UV-A (371 nm) with energy doses that ranged from 3 to 43 $J/cm^2$, which is considered as a moderate dose of energy (40-70 $J/cm^2$) in dermatological phototherapy applications.

Thus, $TiO_2$ has proven to be the most widely used semiconductor metal-oxide photocatalyst due to its strong oxidizing effect, biocompatibility, long-term photostability and low cost. In addition, a pure $TiO_2$ photocatalyst is widely known to be an effective agent against Gram-positive and Gram-negative bacteria upon UV irradiation. However, as noted, the UV energy doses required to promote adequate sterilization are in levels extremely dangerous to human cells and tissues, thus restraining the use of this disinfection technology in the oral cavity. Therefore, enhancing the visible-light-driven antibacterial properties of $TiO_2$ is of value. Several approaches have been tested to re-engineer the $TiO_2$ band gap in order to extend the light absorption of $TiO_2$ into the visible range. Typically, these electronic alterations are based on chemical modifications of the titania crystal lattice by doping, ion implantation, sensitization or coupling with plasmonic noble metal nanoparticles.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the inventive concepts disclosed herein. The patent or application file contains at least one drawing executed in color. Copies of this patent or patent application publication with color drawing(s) will be provided by the Office upon request and payment of the necessary fee.

DETAILED DESCRIPTION

Figure 1:
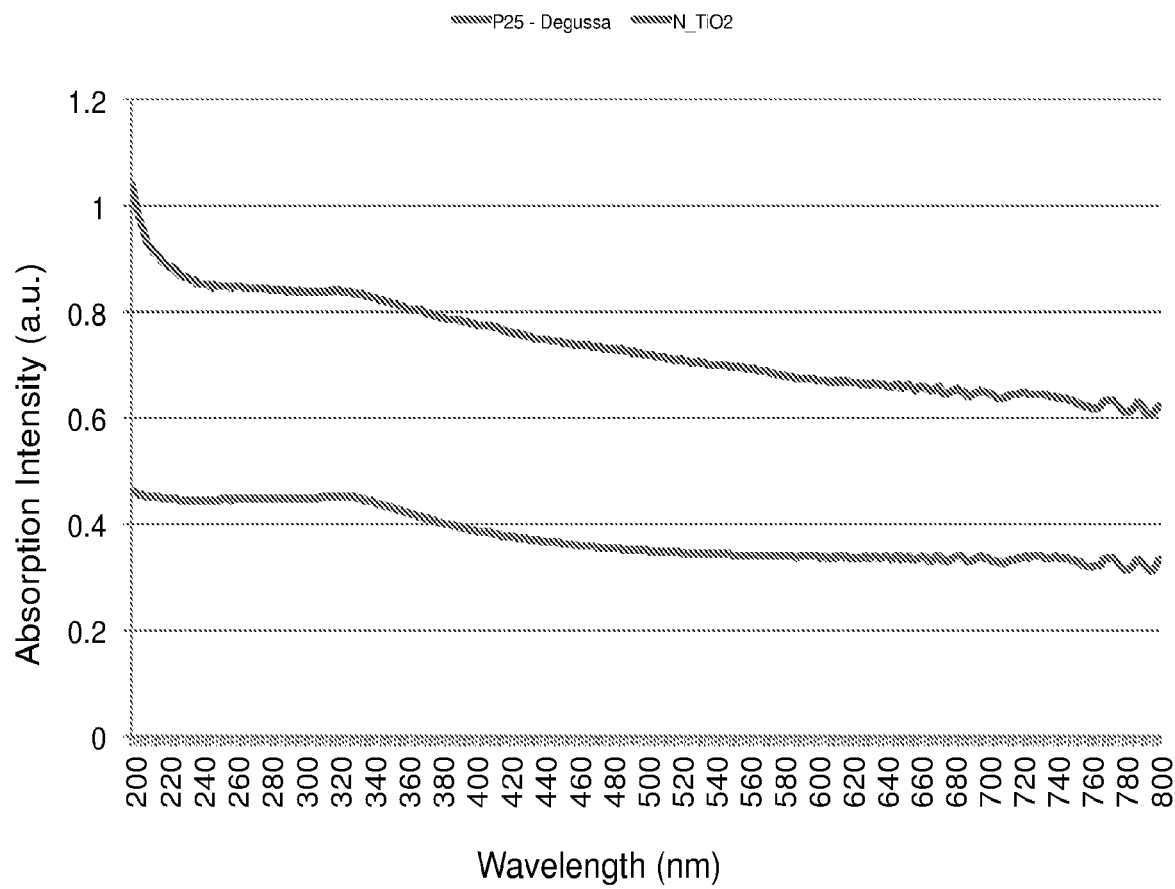
FIG. 1 is a graph of the optical absorption spectrum of titanium dioxide nanoparticles ($TiO_2$ NPs) and nitrogen-doped titanium dioxide nanoparticles (N—$TiO_2$ NPs, a.k.a. N—$TiO_2$) disclosed herein. The graph indicates that N—$TiO_2$ NPs displayed higher optical absorption behavior for the range of wavelengths considered.

A major limitation of adding titanium dioxide nanoparticles ($TiO_2$ NPs) to dental resins has been that the UV wavelengths necessary for activation of $TiO_2$ are or can be dangerous to human cells and tissues. In addition, polymer-based dental materials, when exposed to UV wavelengths, have been demonstrated to undergo significant polymer degradation. As a solution to these problems, the present disclosure describes various novel doped $TiO_2$ nanoparticles (doped $TiO_2$ NPs) for use in polymer-based dental materials (and other materials), such as but not limited to adhesive resins and bonding agents. Examples of such doped $TiO_2$ NPs include but are not limited to nitrogen-doped titanium dioxide ($TiO_{2-x}N_x$ NPs), also referred to herein as N—$TiO_2$ NPs, nitrogen/silver co-doped titanium dioxide (N—Ag—$TiO_2$ NPs), nitrogen/fluorine co-doped titanium dioxide (N—F—$TiO_2$ NPs), and nitrogen/phosphorus or nitrogen/phosphate co-doped titanium dioxide (N—P—$TiO_2$ NPs). The doped $TiO_2$ NPs have use, for example, as antibacterial, bond-promoting, and bioactive materials in polymer-based dental biomaterials. Further, doping and co-doping of titanium dioxide with ions such as nitrogen, fluorine, phosphate, and silver shift the absorption behavior of titanium dioxide from the UV range into the visible spectrum.

Before further describing various embodiments of the compositions and methods of the present disclosure in more detail by way of exemplary description, examples, and results, it is to be understood that the embodiments of the present disclosure are not limited in application to the specific details of methods and compositions as set forth in the following description. The description provided herein is intended for purposes of illustration only and is not intended to be construed in a limiting sense. The inventive concepts of the present disclosure are capable of other embodiments or of being practiced or carried out in various ways. As such, the language used herein is intended to be given the broadest possible scope and meaning; and the embodiments are meant to be exemplary, not exhaustive, and it is not intended that the present disclosure be limited to these particular embodiments. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compositions and methods of production and application and use thereof disclosed herein can be made and executed without undue experimentation in light of the present disclosure. Thus, while the compositions and methods of the present disclosure have been described in terms of particular embodiments, it will be apparent to those of skill in the art that variations may be applied to the formulations, compounds, or compositions and/or methods and in the steps or in the sequence of steps of the method described herein without departing from the spirit and scope of the inventive concepts of the present disclosure.

All patents, published patent applications, and non-patent publications mentioned in the specification are indicative of the level of skill of those skilled in the art to which the present disclosure pertains. Further, all patents, published patent applications, and non-patent publications referenced in any portion of this application (particularly U.S. Ser. No. 62/431,604) are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the tell "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-80 therefore includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, and 80, as well as fractional values within the range, including 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACS, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or +10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance (e.g., reaction) occurs at least 90% of the time, or at least 95% of the time, or at least 98% of the time, or to at least 90%, at least 95%, at least 98%, or at least 99% completion.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" or "bioactive" is meant the ability to modify or affect the physiological system of an organism without reference to how the active agent has its physiological effects. "Antibacterial" refers to the ability to inhibit the growth of and/or to kill bacteria.

As used herein, "pure," or "substantially pure" means an object species (e.g., an imaging agent) is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., an imaging agent) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal, and more particularly, humans. Animals which fall within the scope of the term "subject" as used herein include, but are not limited to, dogs, cats, rats, mice, guinea pigs, chinchillas, horses, goats, ruminants such as cattle, sheep, swine, poultry such as chickens, geese, ducks, and turkeys, zoo animals, Old and New World monkeys, and non-human primates.

"Treatment" refers to therapeutic treatments. "Prevention" refers to prophylactic or preventative treatment measures. The term "treating" refers to administering the composition to a patient for therapeutic purposes.

The terms "therapeutic composition," and "pharmaceutical composition" refer to an active agent-containing composition (e.g., a resin composition comprising doped $TiO_2$ nanoparticles, such as N—$TiO_2$ NPs) that may be administered to or used in a subject by any method known in the art or otherwise contemplated herein, wherein administration or use of the composition brings about an effect or result as described elsewhere herein. In addition, the compositions of the present disclosure may be designed to provide delayed, controlled, extended, and/or sustained effects using formulation techniques which are well known in the art.

The term "effective amount" refers to an amount of an active agent (doped $TiO_2$ nanoparticles) as defined herein (e.g., N—$TiO_2$ NPs) which is sufficient to exhibit a detectable antibacterial and/or bioactive effect or result without excessive adverse side effects (such as toxicity, irritation and allergic response) commensurate with a reasonable benefit/risk ratio when used in the manner of the inventive concepts. The effective amount for a patient will depend upon the type of patient, the patient's size and health, the nature and severity of the condition to be treated or diagnosed, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As noted above, in certain embodiments, the present disclosure is directed to dental compositions, such as but not limited to, dental resins, dental bonding agents, dental adhesives, dental cements, dental restoratives, dentals coatings, dental sealants, acrylic resins, and denture teeth) containing doped or co-doped titanium dioxide nanoparticles such as described herein. The dental compositions may be used in dentistry, for example, as restorative materials, adhesives, bonding agents, cements, sealants, coatings and in the fabrication of partial and complete dentures). These dental compositions have better optical and antibacterial properties when compared to the unaltered commercial dental compositions (e.g., resins) or those comprising undoped $TiO_2$, and have bioactive properties that can improve the service lives of polymer-based dental biomaterials.

Particular applications of the presently disclosed compositions containing doped or co-doped titanium dioxide nanoparticles include the development of dental products such as adhesive resins (e.g., bonding agents) with antibacterial functionalities. However, the resins can also be used in secondary applications after small changes in the functionalization of the nanoparticles. Secondary applications include the development of self-cleaning and antibacterial paints and coatings for health care facilities such as universities, hospitals, private practices, spas and saloons, ambulances (cars, helicopters and planes), and medical devices. These paints and coatings may also be used in public spaces where the control of cross-contamination is important, such as passenger trains, airplanes, cruise-ships, bus and train stations and ultimately in regular businesses and houses.

The presently disclosed doped $TiO_2$ compositions can be used, for example, as or in resin cements (dental and orthopedic), composite resins, denture bases, denture teeth, dental implants, orthodontic brackets and wires, metallic bands and elastomers, catheters, and stents. The presently disclosed antibacterial resins can also be used as antibacterial coatings in hospitals, dental clinics, furniture, equipment, medical devices and hand-held metallic instruments, or for imparting antibacterial properties to indoor and outdoor paints.

In certain non-limiting embodiments, the compositions of the present disclosure which contain the doped $TiO_2$ NPs comprise a resin-based matrix, containing least one monomeric component selected from the group: acrylates, methacrylates, dimethacrylates, epoxies, vinyls and thiols, such as but not limited to ethylenedimethacrylate (EDMA), bisphenol A glycidyl methacrylate (BisGMA), triethyleneglycol dimethacrylate (TEGDMA), 1,6-bis(methacryloxy-2-ethoxycarbonylamino)-2,4,4-trimethylhexane (UDMA), pyromellitic glycerol dimethacrylate (PMGDM), and 2-hydroxyethyl methacrylate (HEMA). The composition may comprise a polymeric material selected from the groups: acrylate resins, methacrylate resins, and dimethacrylate esters resins, epoxy resins, polycarbonate, silicone, polyester, polyether, polyolefin, synthetic rubber, polyurethane, nylon, polystyrene, polyvinylaromatic, polyamide, polyimide, polyvinylhalide, polyphenylene oxide, polyketone, and copolymers and blends thereof. The composition may comprise a solvent selected from the group: water, ethanol, methanol, toluene, ethyl ether, cyclohexane, iso-propanol, chloroform, ethyl acetate, acetone, hexane, and heptanes. An inorganic filler such as silicon dioxide or glass ceramics. The composition may include a coupling agent such as a silane, a photoinitiator such as camphorquinone (CQ), phenylpropanedione (PPD), or lucirin (TPO) for initiating polymerization, and a catalyst to control the rate of the polymerization reaction.

In non-limiting embodiments, the composition may comprise a volume to volume ratio of doped $TiO_2$ to curable resin material in a range of 1% to 80% (v/v), 5% to 50% (v/v), or 10% to 40% (v/v), for example.

EXAMPLES

The present disclosure will now be discussed in terms of several specific, non-limiting, examples and embodiments. The examples described below, which include particular embodiments, will serve to illustrate the practice of the present disclosure, it being understood that the particulars shown are by way of example and for purposes of illustrative discussion of particular embodiments and are presented in the cause of providing what is believed to be a useful and readily understood description of procedures as well as of the principles and conceptual aspects of the present disclosure.

Example 1

Methods

Synthesis of $TiO_2$ Nanoparticles ($TiO_2$ NPs) and doped $TiO_2$ NPs $TiO_2$ NPs for use in the present disclosure can be synthesized using any appropriate method and are not limited to the methods disclosed herein. The NPs can be doped during production of the $TiO_2$ NPs (Process 1), or can be doped after production of the $TiO_2$ NPs (Process 2). For example, the doped $TiO_2$ NPs can be produced using a two-step method wherein $TiO_2$ NPs are produced in the first step (Process 1) and are then processed in a second step (Process 2) to produce the doped $TiO_2$ NPs. In non-limiting embodiments, Process 1 utilizes a solvothermal method, and Process 2 utilizes the nitrogen-doping of the $TiO_2$.

In a non-limiting version of Process 1, titanium (IV) butoxide (TB, 97%) (5-10 mmol) was added to a mixture of X mmol oleic acid (OA, 90%), Y mmol oleylamine (OM, 70%), and 100 mmol absolute ethanol (X+Y=50). X and Y can be varied while leaving the molar ratio of titanium n-butoxide (TB) and surfactants unchanged (i.e., TB/(OA+OM)=1:10) to gain different OA/OM ratios, which lead to the formation of different shapes of NPs. For example, to synthesize $TiO_2$ with truncated rhombic shape, 5 mmol of TB was added to a mixture of 25 mmol OA, 25 mmol OM, and 100 mmol absolute ethanol. The obtained mixture in a 40 mL Teflon cup was stirred for 10 min before being transferred into a 100 mL Teflon-lined stainless steel autoclave containing 20 mL of a mixture of ethanol and water (96% ethanol, v/v). The concentration of ethanol was used at the azeotropic point so that the amount of water vapor did not change much during the crystallization process. The system was then heated at 180° C. for 18 h. The obtained white precipitates were washed several times with ethanol and then dried at room temperature. The as-synthesized $TiO_2$ NP products were dispersed in nonpolar solvent, such as toluene. $TiO_2$ NPs synthesized by varying the OA/OM molar ratio, When the OA/OM mole ratio is 4:6, rhombic-shaped $TiO_2$ NPs with uniform size are obtained. By increasing the OA/OM molar ratio to 5:5, smaller $TiO_2$ NPs with truncated rhombic shape can be produced. A further increase of this ratio up to 6:4 leads to the formation of spherical particles with an average size of 13 nm.

In a particular non-limiting example of Process 1, a solution comprised of 1.7 g of Ti(IV)-butoxide (Aldrich, 97%), 4.6 g ethanol (Decon Labs, 100%), 6.8 g oleylamine (Aldrich, 70%), and 7.1 g oleic acid (Aldrich, 90%) was prepared, then mixed with 20 mL of 4% $H_2O$ in ethanol (18-MΩ Milli-Q; Decon Labs). Each solution was clear before mixing, but the final mixture immediately clouded due to formation of micelles and likely some hydrolysis. This solution was then split into two portions (around 20 mL/portion), and each portion was placed into a high-pressure reaction vessel (Paar Series 5000 Multiple Reactor System) and reacted at 180° C. for 24-hours. The vessels were stirred via external magnetic field and Teflon-coated stir bars. The reaction vessels were Teflon-lined. Upon cooling, the solutions were decanted and rinsed 3 times with anhydrous ethanol to remove extraneous surfactants resulting in pure $TiO_2$ NPs which were readily dispersible into 20-30 mL ethanol, but did not form clear solutions. The $TiO_2$ NPs formed were stored in ethanol.

In a particular non-limiting embodiment of Process 2 for making doped $TiO_2$ NPs, a portion of the $TiO_2$ NPs in ethanol (manufactured in Process 1) are then reacted with an equal volume of triethylamine (Sigma-Aldrich Co., LLC.), also using the high-pressure reaction vessel, at 140° C. for 12 hours. Upon cooling the now-nitrogen-doped $TiO_2$ NPs (N—$TiO_2$ NPs) are rinsed 3 times with anhydrous ethanol. The exact concentration of $TiO_2$ in ethanol/triethylamine varies, but in every instance there is an excess of triethylamine. The final N—$TiO_2$ NP ethanol solution yields a gravimetrically-determined concentration of particles typically in the range of 35 mg/mL. In at least certain embodiments, the N/Ti molar ratio of the N—$TiO_2$ NPs was in a range of 0.1% to 3.4%.

Synthesis of Co-Doped-$TiO_2$ NPs

Nitrogen and Silver co-doping. N—Ag—$TiO_2$ NPs can be formed following the reaction steps of Process 1 using Ti(IV)-butoxide. Ag is provided by adding silver acetylacetonate and N is provided using tetramethyl ammonium hydroxide as the dopant sources in a wt:wt:wt N:Ag:Ti ratio of, for example, 1:1:18, which provides a 5%/5%/90% N/Ag/Ti composition. For example in one embodiment, components sufficient to provide 0.085 g N and 0.085 g Ag can be combined with a component comprising Ti (e.g., Ti(IV)-butoxide) are used. The $TiO_2$ NPs form as in Process 1 but with the N and Ag dopants in place.

Nitrogen and Fluorine co-doping. N—F—$TiO_2$ NPs can be formed following the reaction steps of Process 1 using Ti(IV)-butoxide. F and N are provided by adding ammonium fluoride as the dopant sources in a wt:wt:wt N:Ag:Ti ratio of, for example, 1:1:18, which provides a 5%/5%/90% N/F/Ti composition. For example in one embodiment, components sufficient to provide 0.085 g N and 0.085 g F can be combined with a component comprising Ti (e.g., Ti(IV)-butoxide) are used. The $TiO_2$ NPs form as in Process 1 but with the N and F dopants in place.

Phosphate coating of $TiO_2$ NPs. In this variation, undoped $TiO_2$ NPs, N—$TiO_2$ NPs, or co-doped $TiO_2$ NPs are treated to provide a coating of phosphate on the outer surface of the particles. The nanoparticles are dispersed into commercial phosphate buffered saline (PBS), which is a neutral pH solution of sodium phosphate. Upon reaction as usual, the particles become phosphate-derivatized and are amenable to further mineralization. The phosphate coated $TiO_2$ NPs are designated herein as P—$TiO_2$ NPs. The phosphate coated N—$TiO_2$ NPs are designated herein as N—P—$TiO_2$ NPs. The phosphate coated N—Ag—$TiO_2$ NPs are designated herein as N—Ag—P—$TiO_2$ NPs. The phosphate coated N—F—$TiO_2$ NPs are designated herein as N—F—P—$TiO_2$ NPs.

Characterization of N—$TiO_2$ NPs

UV-VIS Spectroscopy $TiO_2$ (P25, Evonik Degussa GmbH, Germany) and N—$TiO_2$ (Oak Ridge National Laboratory, TN) nanoparticles in ethanol suspension were individually characterized regarding its optical absorbance with a Cary®50 (Agilent Technologies, Santa Clara, CA) spectrophotometer using the transmittance method. Aliquots (20 μL) of each material (either P25 or N—$TiO_2$, 40 mg/mL in ethanol) were individually placed in a quartz microcell. Each sample was then placed inside of the spectrophotometer's chamber between the light source and the photodetector and the intensity of light that reached the photodetector was measured from 190 nm-900 nm in 2 nm increments (FIG. 1).

Scanning Electron Microscopy (SEM)

Figure 2:
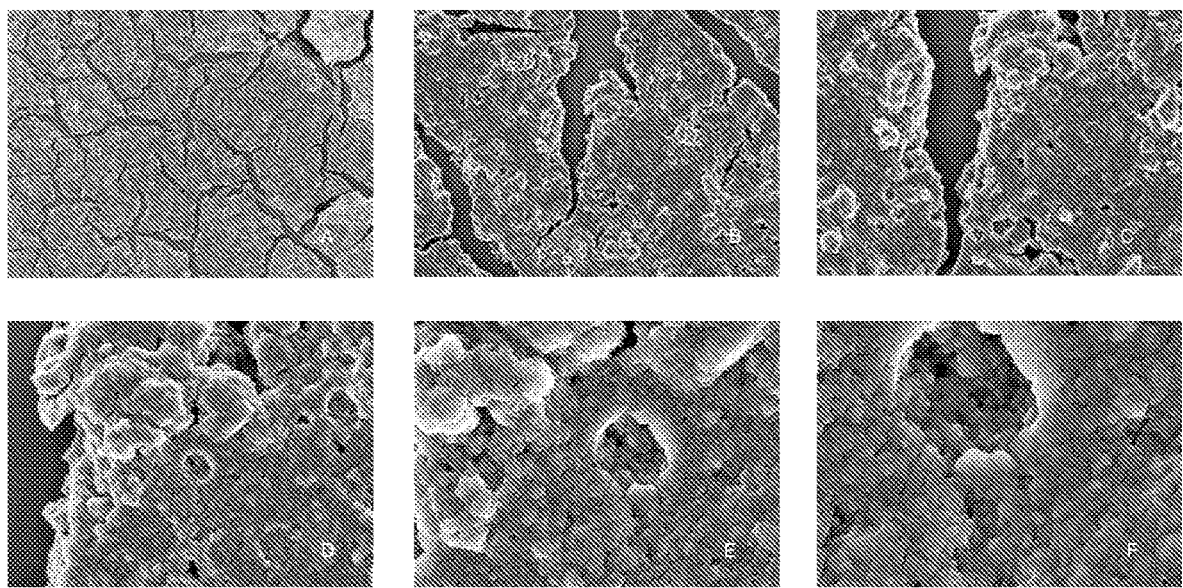
FIG. 2 shows scanning electron microscope (SEM) images demonstrating intense agglomeration of N—$TiO_2$ (40 mg/mL, Oak Ridge National Laboratory). A-F show magnifications of 500×, 2.50K×, 5.00K×, 10.00K×, 25.00K× and 50.00K×, respectively. It is possible to observe in the images of higher magnification (D-F) that the strong agglomeration pattern promoted the formation of layered structures potentially several hundred microns thick (Z direction).
Figure 3:
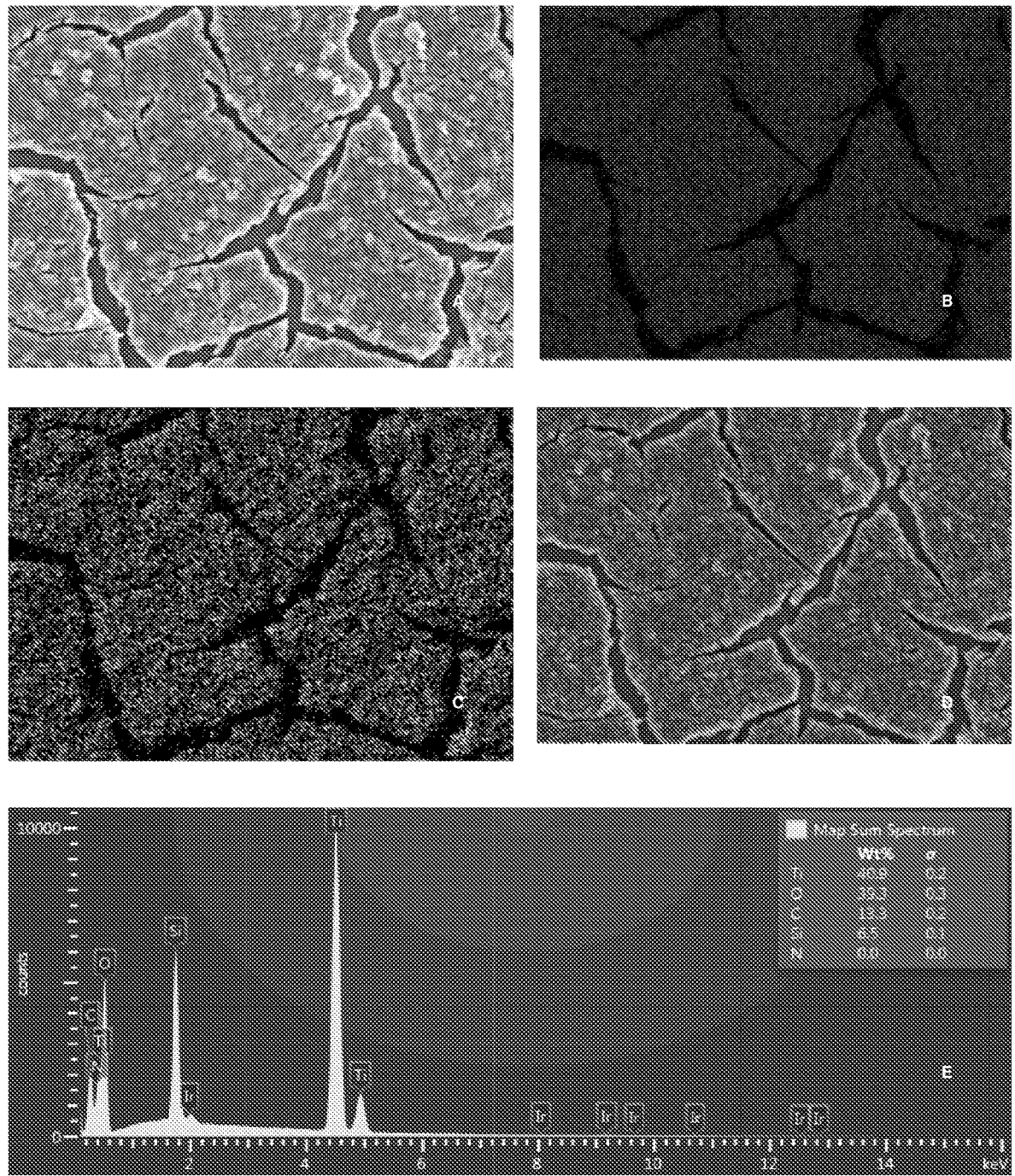
FIG. 3 shows energy dispersive X-rays spectroscopy (EDS) images. (A) Representative image of N—$TiO_2$ using X-Rays. (B) Mapping image of the titanium (Ti) presence in the investigated sample. (C) Mapping image of the oxygen (O) presence in the investigated sample. (D) EDS layered image demonstrating the Ti and O mapping. In the layered image it is also possible to observe the presence of carbon and silicon. (E) Compositional analysis of the investigated sample. Visible peaks confirming the presence of elements and relative amounts in the sample investigated.

Aliquots (5 μL) of N—$TiO_2$ NPs suspended in ethanol in the as-synthesized concentration (200 proof, 40 mg/mL, Oak Ridge National Laboratory, USA) were placed onto a polished silicon wafer. N—$TiO_2$ NP samples were air-dried in room temperature until all the solvent had been evaporated. Individual specimens were then mounted onto standard aluminum SEM pin stubs (diameter ⅛") and were sputter coated with a thin-layer (~4 nm) of iridium using a sputter coater (K575D, Emitech Sample Preparation, UK) prior to the imaging process. Adhesive samples containing 50, 67 and 80% (v/v) were mounted directly onto standard aluminum SEM pin stubs using double-sided carbon tape and silver paste for electrical grounding to the stub. The adhesive samples were sputter coated using the same procedures described for the N—$TiO_2$ in suspension. Both, N—$TiO_2$ NPs in suspension and immobilized in dental adhesive resins were imaged using a Zeiss Neon 40 EsB SEM at 5 kV (FIG. 2). Energy dispersive X-ray spectroscopy (EDS) and EDS compositional mapping was performed using an Oxford INCA 250 microanalysis system with an analytical drift detector at 15 kV (FIG. 3).

Transmission Electron Microscopy (TEM)

N—$TiO_2$ NPs suspended in ethanol (100%, 0.032 mg/mL, Oak Ridge National Laboratory, USA) were dispersed by brief sonication in an ultrasound bath (Bransonic 220, Branson Ultrasonics, USA). A drop of suspended $TiO_2$ NPs was placed on holey carbon coated copper grids. The drop was allowed to adsorb for 1-2 min, then wicked with filter paper to remove excess fluid, and dried before viewing in a JEOL 2000FX transmission electron microscope. Images were made on Carestream® Kodak® electron image films SO-163 (Eastman Kodak Company, USA) and digitized with an Epson Perfection V750-M Pro scanner (Epson America, Inc.

Figure 4:
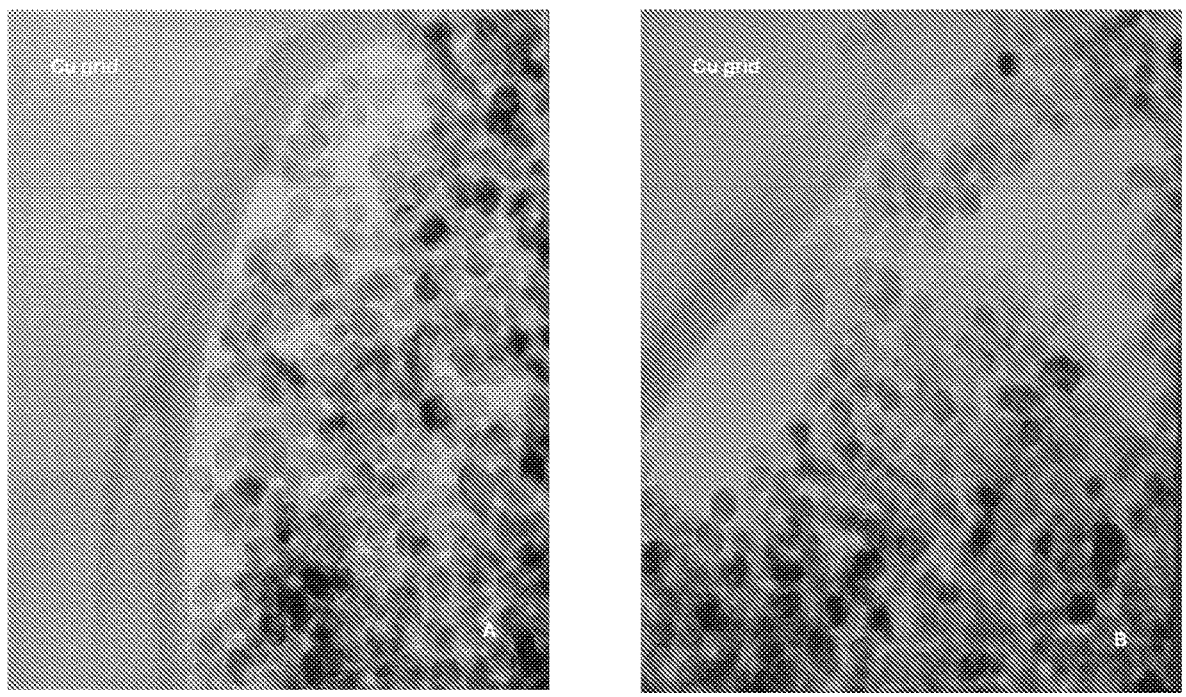
FIG. 4 shows transmission electron microscope (TEM) images (500K×) of N—$TiO_2$ NPs samples diluted in ethanol (1:1250, 200 proof). (A-B) Representative images confirming the spherical shape of the nanoparticles, with smooth surface and sizes around 10 nm. It is also possible to observe that nanoparticles tend to aggregate even in a very diluted sample. TEM images also display the presence of the copper grid used during the images acquisition. (C) Compositional analysis performed during the TEM characterization.
Figure 4:
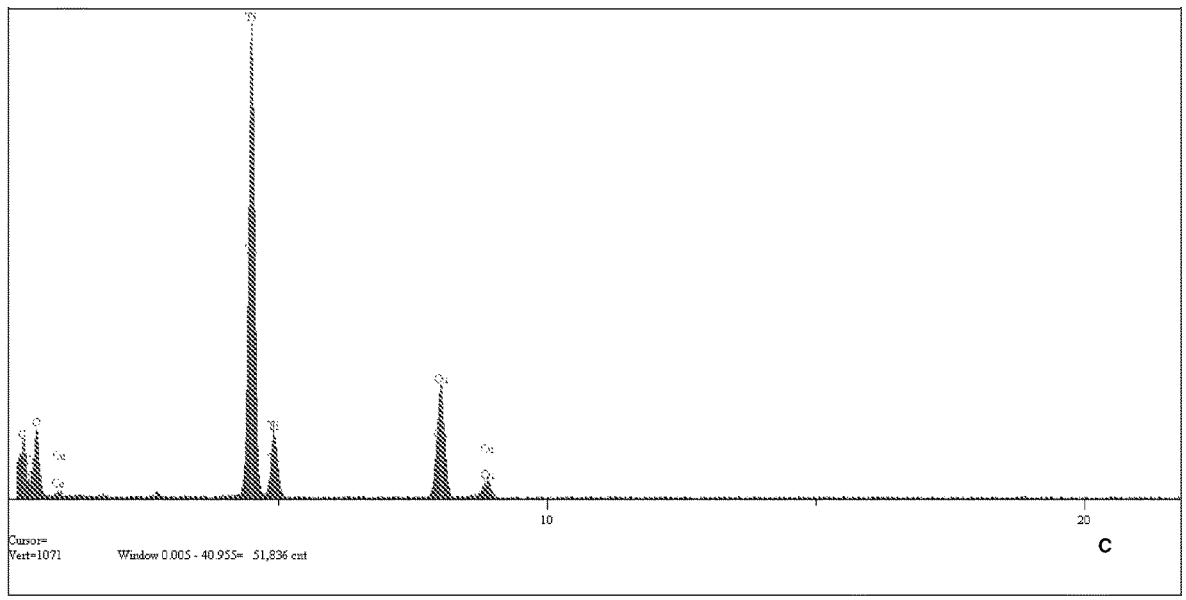

USA). X-ray spectra were collected using a Kevex thin window detector and EDS software (IXRF Systems Inc., USA) (FIG. 4).

Specimen Fabrication

Disk shaped specimens (diameter=12.00 mm, thickness ≅15 μm) of OptiBond Solo Plus (OBSP) adhesive resin (Kerr Corp., USA) and experimental adhesive resins containing 50, 67 and 80% (v/v) of N—TiO$_2$ NPs, were manually fabricated by individually dispensing 10 μL of each material onto the surfaces of separated glass coverslips (No. 2, VWR International, LLC). Then both the unaltered and experimental adhesive resins were uniformly spread over glass coverslips using disposable flexible applicators (Kerr Corp., USA) and were polymerized using blue light irradiation (1000 mW/cm$^2$, 1 min) emitted from a broadband LED light-curing unit (VALO, Ultradent Products, Inc., USA). Specimens of both unaltered and experimental adhesive resins were then UV-sterilized (254 nm, 800,000 μJ/cm$^2$, UVP Crosslinker, model CL-1000, UVP, USA). Similarly, P—TiO$_2$ NPs, N—P—TiO$_2$ NPs, N—Ag—TiO$_2$ NPs, N—Ag—P—TiO$_2$ NPs, N—F—TiO$_2$ NPs, and N—F—P—TiO$_2$ NPs can be mixed with adhesive resins including but not limited to OBSP to form doped-TiO$_2$ dental resins.

Bacterial Strain

*Streptococcus mutans* strain UA159 (JM10::pJM1-ldh, luc+, Spr, luc under the control of the ldh promoter) was utilized for this project. The selection of antibiotic-resistant colonies was performed on TH plates (Todd-Hewitt, BD Difco, USA) supplemented with 0.3% yeast extract (EMB, Germany) and 800 μg/mL of spectinomycin (MP Biomedicals, USA). The plates were incubated under anaerobic conditions at 37° C. for 48 h.

Antibacterial Behavior of N—TiO$_2$ NPs in Suspension

In order to assess the antibacterial efficacy of the N—TiO$_2$ in ethanol suspension (200 proof, 40 mg/mL, Oak Ridge National Laboratory, USA), *S. mutans* biofilms were grown in sterile microcentrifuge tubes (Safe-Lock Tubes, Eppendorf North America, USA). Planktonic cultures of *S. mutans* (UA159-ldh, JM10) were grown in THY culture medium at 37° C. for 16 hours. Planktonic cultures having optical density (OD$_{600}$) levels≥0.900 were used as inoculum to grow the biofilms. A 1:500 dilution of the inoculum was added to 0.65×THY+0.1% (w/v) sucrose biofilm growth medium.

Inoculum aliquots (1.00 mL) were added to separate sterile microcentrifuge tubes and biofilms were grown for 24-hours (static cultures, anaerobic conditions, 37° C.). After the growth period, biofilms were replenished with 1.00 mL of fresh 1×THY+1% (w/v) glucose culture medium and were incubated at 37° C. for 1 hour. Replenished biofilms (n=15/group/irradiation condition) were then exposed to the nanoparticles diluted in growth media [1×THY+1% (v/v)] in the concentrations of 19%, 25% and 30% (v/v) with or without blue light irradiation (1000 mW/cm$^2$, 1 min) provided by a commercially available broadband LED light-curing unit (VALO, Ultradent Products, Inc., USA). Biofilms that were not exposed to the nanoparticles comprised our negative control (n=45). Positive control groups (n=15/concentration) were comprised by biofilms that were exposed to ethanol aqueous solutions (200 proof, AAPER Alcohol and Chemical Co., Shelbyville, KY) in concentrations of 19%, 25% and 30% (v/v) with or without light irradiation (1000 mW/cm$^2$, 1 min). Following the treatment, the suspension containing either N—TiO$_2$ NPs in suspension or ethanol aqueous solution was carefully aspirated. Immediately after, biofilms were replenished with 1.00 mL of fresh 1×THY+1% (w/v) glucose sterile culture medium. The microcentrifuge tubes containing the replenished biofilms were then sonicated to facilitate the removal of the adherent biomass using a sonicator (Q700 sonicator, QSonica, USA) connected to a water bath (4° C.; 4 cycles of 1 minute, 15 seconds interval between cycles; power 230±10 W, total energy ≈ 78 kJ).

Antibacterial behavior of N—TiO$_2$ NPs immobilized in dental adhesive resins

In order to assess the antibacterial efficacy of experimental adhesive resins containing 50%, 67% and 80% (v/v) of N—TiO$_2$ NPs (Oak Ridge National Laboratory, USA), *S. mutans* biofilms were grown against the surfaces of sterile specimens of both unaltered and experimental adhesive resins. Planktonic cultures of *S. mutans* (UA159-ldh, JM10) were grown in THY culture medium at 37° C. for 16 hours. Planktonic cultures having optical density (OD$_{600}$) levels≥0.900 were used as inoculum to grow the biofilms. A 1:500 dilution of the inoculum was added to 0.65×THY+0.1% (w/v) sucrose biofilm growth medium. Inoculum aliquots (2.5 mL) were dispensed into the wells of sterile 24-well microtiter plates (Falcon, Corning, USA) containing sterile specimens. Biofilms were grown for either 3- or 24-hours (static cultures, anaerobic conditions, 37° C.) with or without continuous light irradiation provided by a prototype LED device (410±10 nm, 3 h irradiation=38.75 J/cm$^2$, 24 h irradiation=310.07 J/cm$^2$).

After the growth period, biofilms were replenished with 2.5 mL of fresh 1×THY+1% (w/v) glucose culture medium and were incubated at 37° C. for 1 hour. Replenished biofilms were transferred into individual sterile polypropylene tubes (3 mL, ConSert Vials, Thermo Fisher Scientific, USA) containing 1.0 mL of fresh 0.65×THY+0.1% (w/v) sucrose medium. Vials containing the specimens were sonicated to facilitate the removal of the adherent biomass using a sonicator (Q700 sonicator, QSonica, USA) connected to a water bath (4° C.; 4 cycles of 1 minute, 15-second interval between cycles; power 230±10 W, total energy ≈ 78 kJ).

Colony-Forming Units (CFU/mL)

Biofilms grown either in the microcentrifuge tubes or on the surfaces of both unaltered and experimental dental adhesive resins were sonicated to allow the antibacterial efficacy assessment using the colony-forming units method. Immediately after sonication procedures, inoculum aliquots (10 μL) from each specimen were diluted in 90 μL of 0.65× THY+0.1% (w/v) sucrose sterile culture medium. Serial dilutions were then carried out in 0.65×THY+0.1% (w/v) sucrose sterile culture medium for all samples using a multi-channel pipette (5-50 μL, VWR, USA). Aliquots (10 μL) of each dilution were then plated in triplicate (total: 30 μL/sample/dilution) using THY plates supplemented with 800 μg of spectinomycin.

Staining and Confocal Laser Scanning Microscopy

A separate set of specimens was fabricated as described above. Biofilms were then grown on the surfaces of unaltered and experimental adhesive resins, using the conditions above in preparation for staining and confocal microscopy. The biofilms on all specimens were stained using BacLight™ LIVE/DEAD fluorescent stains (1.67 μM each of Syto 9 to stain live cells and propidium iodide to stain dead/damaged cells, Molecular Probes, USA) and kept hydrated prior to confocal microscopy. The full thickness of biofilms on all specimens was imaged by confocal microscopy at three randomly selected locations per specimen, in order to gain a representative sample for each specimen, using a Leica TCS SP2 MP confocal laser scanning microscope (CLSM) with Ar (488 nm) and He/Ne (543 nm) lasers for excitation of the fluorescent stains. A 63× water immersion microscope objective lens was used and serial optical sections were recorded from the bottom of the specimen to the top of the biofilm at 0.6 µM intervals in the z-direction. Representative 3-D reconstruction images of live and dead/damaged cells in the 24-hour biofilms grown on adhesive resins were generated using Velocity software (Version 4.4.0, Velocity Software solutions Pvt. Ltd., India) to facilitate visualization of biofilm distribution in all groups investigated.

Contact Angle Goniometry

A separate set of specimens (n=4/group/concentration) was fabricated as described above in preparation for the contact angle goniometry at oral temperature (37° C.). Immediately after fabrication, specimens of each group were left undisturbed (10 min) inside of the environmental chamber of a contact angle goniometer (OCA15-Plus, Dataphysics Instruments, Germany) for thermal equilibration prior to testing. The wettability of water was tested at oral temperature by displacing a 2 µL drop of ultrapure pure water onto four random locations of each specimen (16 drops/group). The profiles of the axisymmetric drops were recorded using a high-speed and high-definition CCD camera (1 min, 25 frames/sec). The evolution of drop profiles over time was analyzed using the SCA20 software (Dataphysics Instruments, Germany) and the Laplace-Young equation was used to calculate the contact angles at time=0 s ($\theta_{INITIAL}$) and time=59 s ($\theta_{FINAL}$).

Results

UV-Vis Spectroscopy

FIG. 1 represents the UV-vis spectroscopy results for both the undoped and nitrogen-doped titanium dioxide nanoparticles. It is possible to observe that doped samples displayed higher absorption levels throughout the range of wavelengths considered, which confirms that nitrogen was successfully incorporated into the crystal lattice of titanic.

SEM, EDS and TEM Characterization of N—$TiO_2$ NPs Suspended in Ethanol

FIG. 2 represents the SEM pictures of the N—$TiO_2$ NPs at different magnifications (500× to 50,000×). Even though it is possible to observe a strong agglomeration behavior of the nanoparticles in the as-synthesized concentration (40 mg/mL in 100% ethanol), these pictures indicate that nanoparticles fabricated by the solvothermal method described above have an approximately spherical shape, smooth surfaces and most of the nanoparticles exhibit some faceting.

FIG. 3 represents the EDS pictures of the compositional analysis of the N—$TiO_2$ NPs in the as-synthesized concentration (40 mg/mL). The mapping of elements indicates large quantities of titanium (Ti), oxygen (O), carbon (C) and silicon (Si). The visible peaks present in the EDS compositional spectrum confirm the presence, and the relative amounts (in wt %) of the elements in the samples investigated. The results of the analysis of compositional characterization of the N—$TiO_2$ NPs by EDS revealed that Ti (40.9%), O (39.3%), C (13.3%) and Si (6.5%) were the major components found in N—$TiO_2$ NP samples. The presence of silicon is related with the wafer substrate in which the samples were imaged. However, under the conditions used herein the doping element (nitrogen) could not be mapped. It is believed that the combination of factors like the low atomic number of nitrogen (Z=7), and the complete overlap between the Ti Lλ (0.395 keV) and the N Kα (0.392 KeV) peaks made the mapping of nitrogen in the N—$TiO_2$ NP samples impossible. The characterization of light elements such as Be, B, N and F is difficult due to their low photon energies, low yield of x-rays and low energy to noise ratio. FIG. 4 represents the TEM pictures (500,000× magnification) and compositional analysis of N—$TiO_2$ NPs. The TEM images presented confirm the SEM findings regarding the morphologies of the N—$TiO_2$ NPs and demonstrated that synthesized nanoparticles had sizes varying around 10 nm. In addition, it is also possible to observe that even for a very diluted sample (1:1250 in 100% ethanol) the nanoparticles still display a strong agglomeration behavior.

Figure 5:
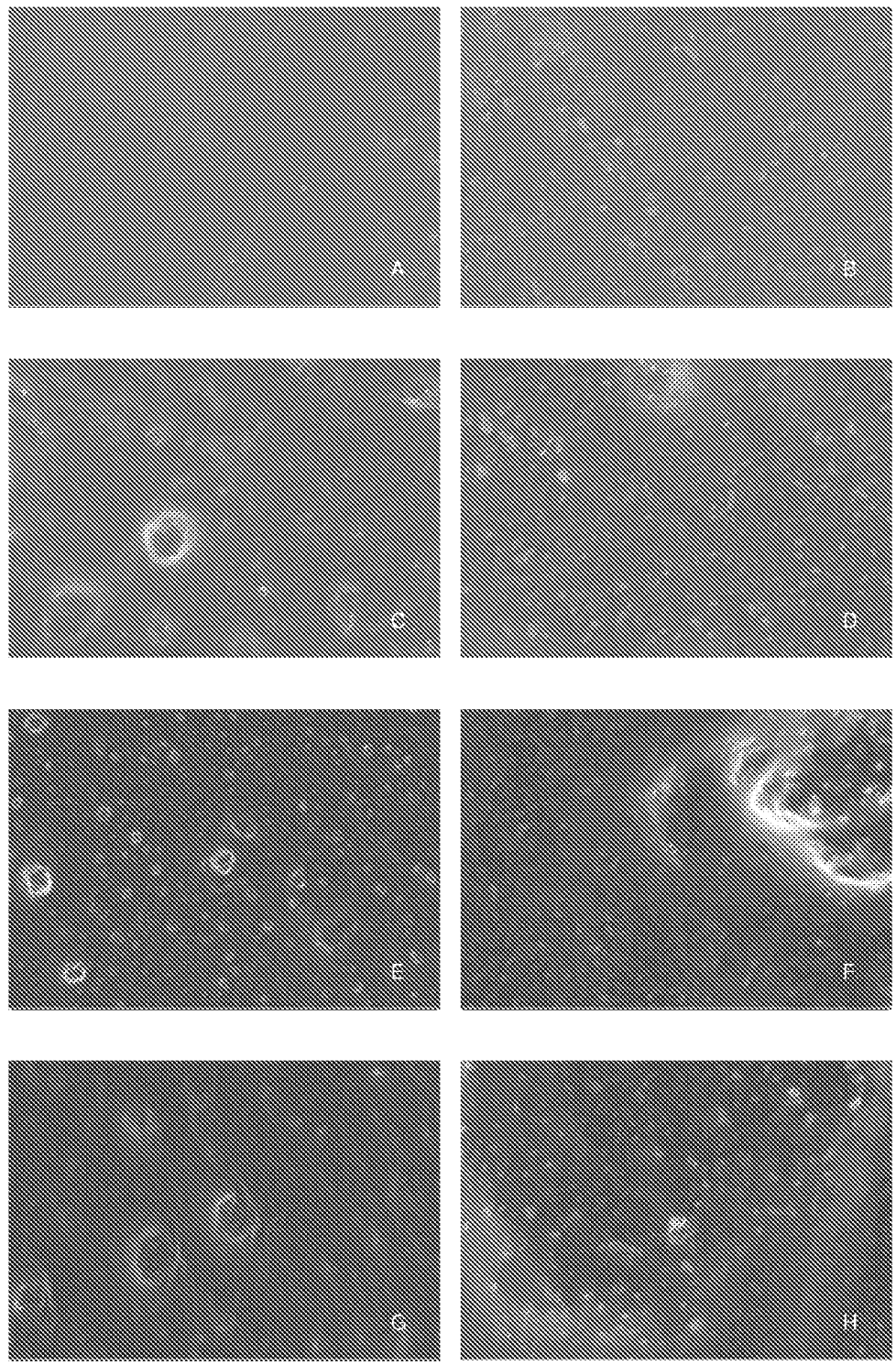
FIG. 5 shows SEM images (500× and 5,000× magnification) of thin-films (thickness≅15 μm) fabricated using a control adhesive [OptiBond Solo Plus (OPTB)] vs. experimental dental adhesive resins containing N—$TiO_2$ NPs concentrations of 50%, 67% and 80% (v/v). Experimental adhesives were OPTB plus a quantity of N—$TiO_2$ NPs. The SEM analysis confirmed the successful incorporation of N—$TiO_2$ NPs in the polymer matrix by revealing the presence of increasing amounts of particles at the surface level.

SEM and EDS Characterization of N—$TiO_2$ NPs Immobilized in Dental Adhesive Resins FIG. 5 represents the SEM pictures (500× and 5,000× magnifications) of both unaltered and experimental dental adhesive resins containing 50%, 67% or 80% (v/v) of N—$TiO_2$. It is possible to observe (FIG. 5C-H) that adhesive resins containing higher N—$TiO_2$ NP concentrations resulted in materials with rougher surfaces due to the higher presence of particles at the surface level. In addition, it is possible to observe that materials containing 67% and 80% (v/v) presented particles (FIG. 5E-H) that were not covered by the adhesive matrix when compared to the remaining groups. This finding can be observed by the presence of circular-shaped particulates of very intense brightness.

Figure 6:
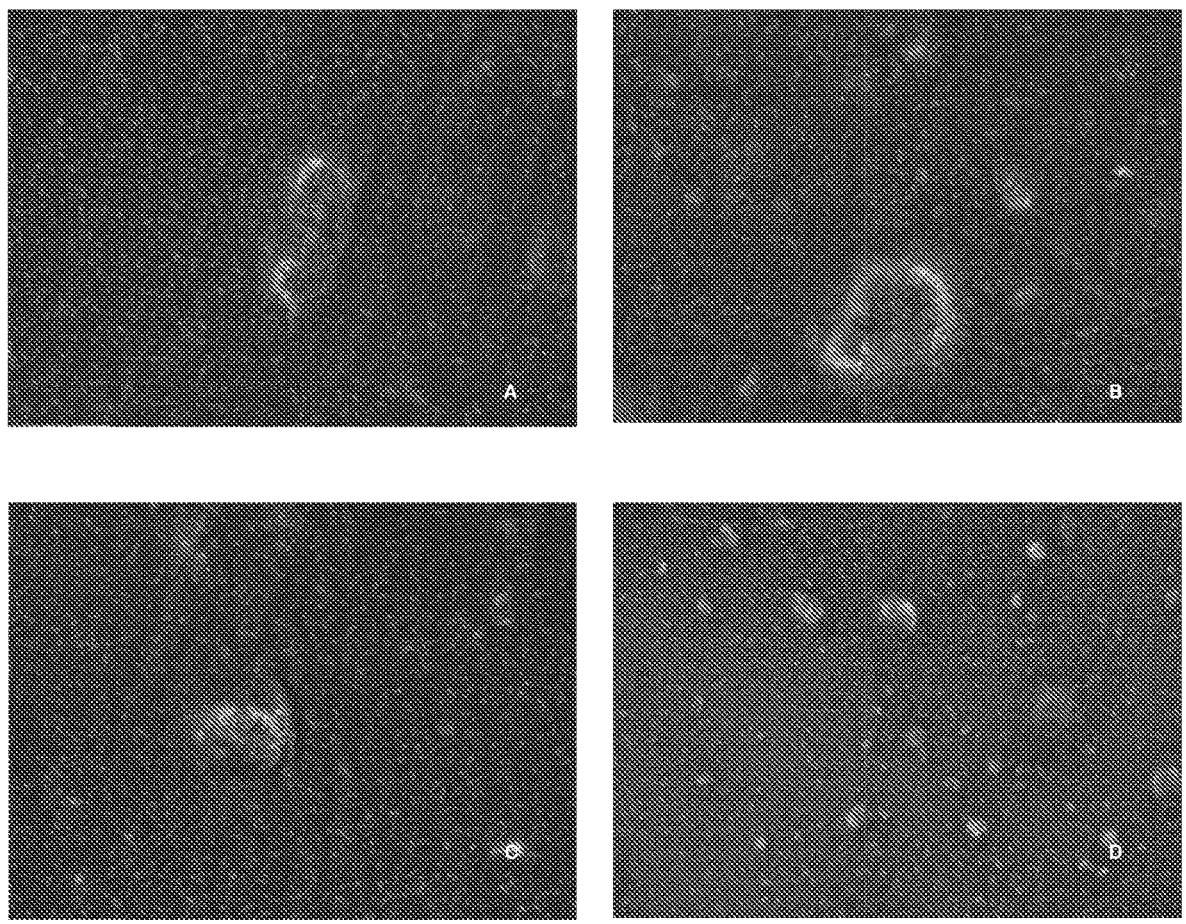
FIG. 6 shows EDS layered images of the elemental compositional analysis for barium (Ba), silicon (Si), oxygen (O), carbon (C), titanium (Ti) and aluminum (Al). (A) OptiBond Solo Plus (OPTB), (B) Experimental adhesive resin with 50% (v/v) of N—$TiO_2$ NPs, (C) Experimental adhesive resin with 67% (v/v) of N—$TiO_2$ and (D) Experimental adhesive resins with 80% (v/v) of N—$TiO_2$ NPs.

FIG. 6 represents the results of the compositional analysis of both unaltered and experimental dental adhesive resins. It is possible to observe on image A that the elements composing the unaltered adhesive resins were mainly barium, silicon, oxygen and carbon, which is in agreement with the composition expected for an unaltered dental adhesive resin. Images B to D demonstrate increasing amounts of titanium and oxygen, which can be observed on the images by the presence of increasing amounts of pink (Ti) and yellow dots (O).

Contact Angle Goniometry

Figure 7:
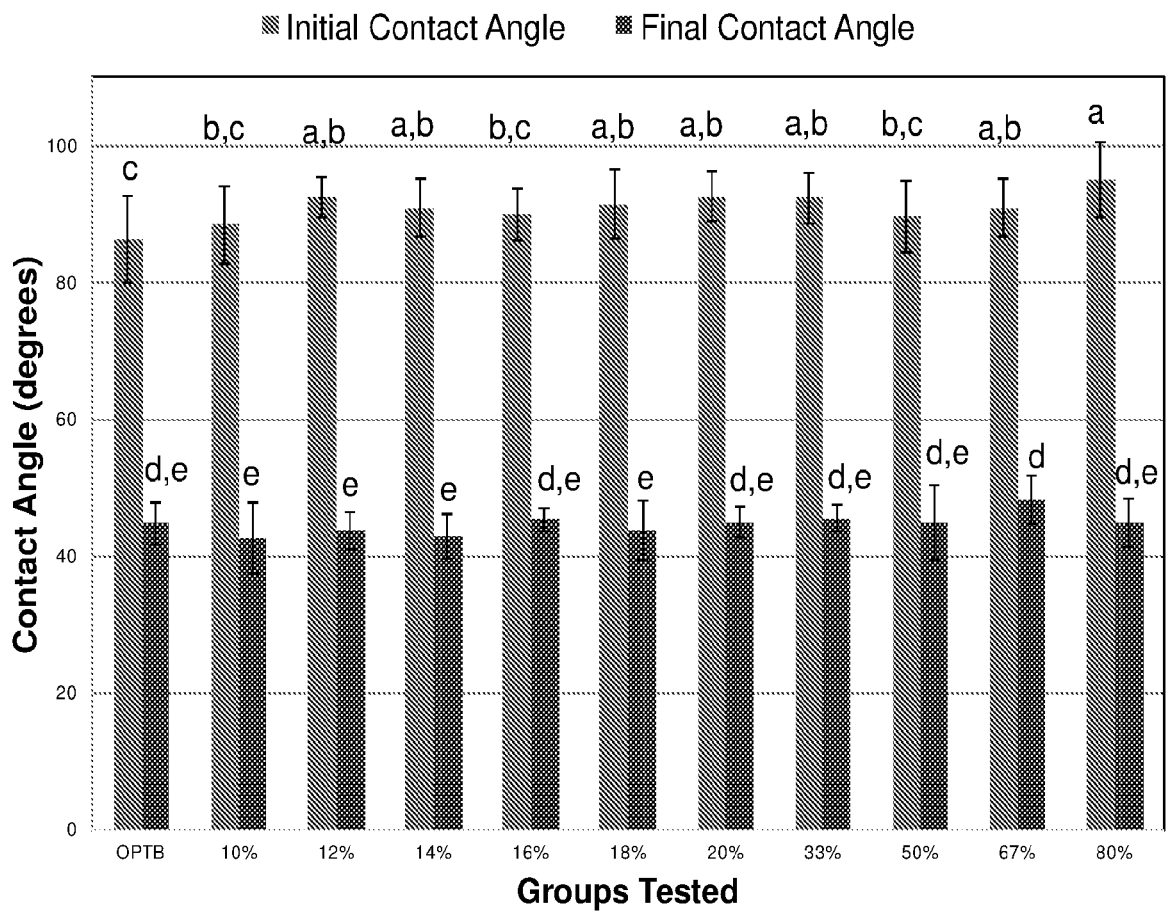
FIG. 7 is a graph showing the effect of N—$TiO_2$ NPs concentration on contact angle, a measure of wettability of a surface. Initial ($\theta_{INITIAL}$, Blue bars) and final ($\theta_{FINAL}$, Red Bars) represent water wettability on dental adhesive resins at oral temperature (37° C.). Different letters denote groups that present differences that were statically significant.

The results obtained from the assessment of the wettability of water at times 0 s ($\theta_{INITIAL}$) and 59 s ($\theta_{FINAL}$) on both, unaltered and experimental dental adhesive resins, are presented in a self-explanatory graph of mean and standard deviation values (FIG. 7). The results demonstrate that, independent of the group considered, initial contact angles (t=0 s) had values that were consistently higher than the values of the final contact angles (t=59 s). The SNK post hoc test demonstrates that similar initial contact angle values were obtained in all groups tested. Although final contact angles were smaller in value than initial contact angles, a similar trend of wettability behavior could still be noticed, where no significant differences among the groups tested could be observed.

Antibacterial Behavior of N—$TiO_2$ NPs in Suspension

Figure 8:
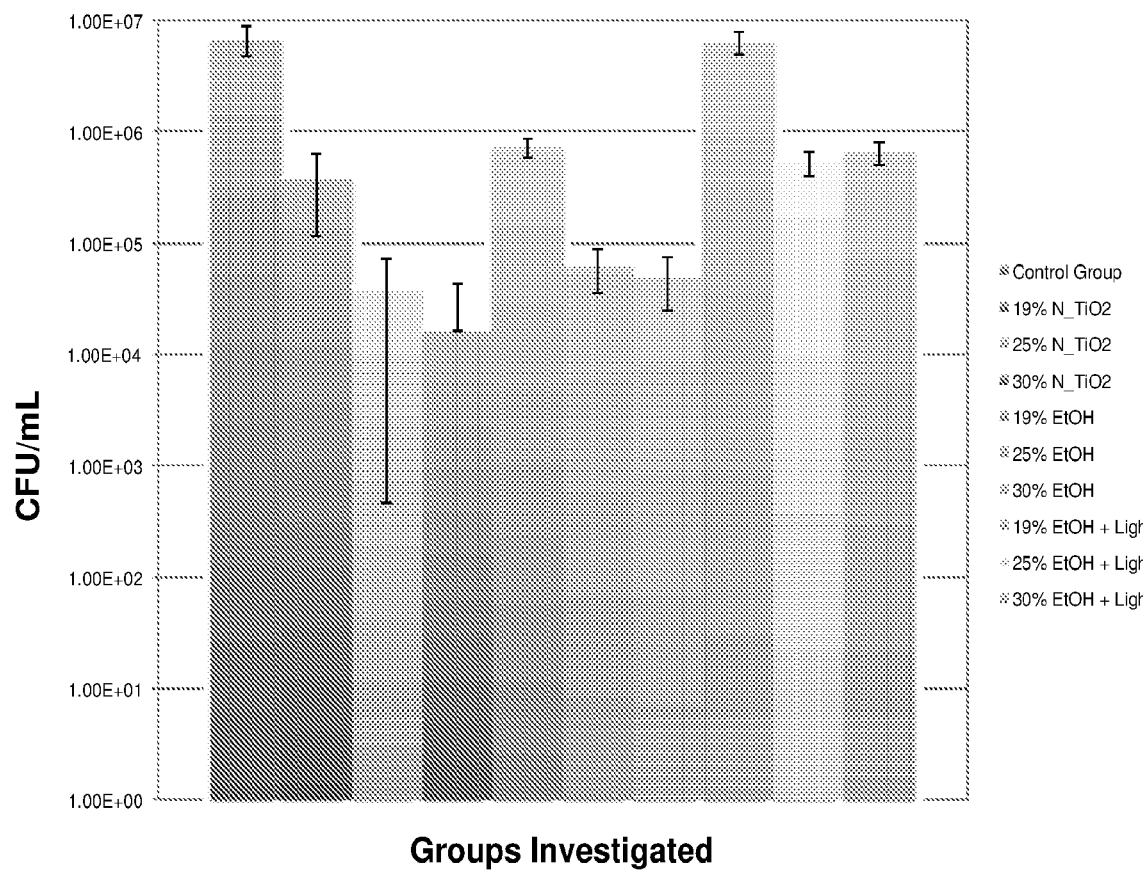
FIG. 8 is a graph showing antibacterial efficacy of the groups tested. Individual columns represent mean and standard deviation values. Lower colony forming units per ml (CFU/mL) values indicate groups having higher antibacterial behavior.

The results of the antibacterial activity of N—$TiO_2$ NPs against *S. mutans* biofilms grown in microcentrifuge tubes were determined by the colony-forming units (CFU/mL) method and are presented in FIG. 8 as mean and standard deviation values, and % survival vs. % treatment efficacy (Table 1). The results demonstrated that all N—$TiO_2$ NPs and ethanol concentrations tested (19%, 25% or 30% (v/v)] significantly decreased the viability of *S. mutans* biofilms when compared to the control group (intact biofilms). It is also possible to observe that the combination of ethanol and visible light produced viability results that were higher when compared to both experimental groups (N—$TiO_2$ NPs or ethanol only) and were comparable to the control group (intact biofilms), which suggest that blue light may act as a biomodulator in situations of low cytotoxic stress.

TABLE 1

Survival rate and Treatment efficacy

| | Survival rate (%) | Treatment efficacy (%) |
|---|---|---|
| Control Group (n = 45) | 100.00% | 0.00% |
| 19% (v/v) N_TiO$_2$ (n = 15) | 5.58% | 94.42% |
| 25% (v/v) N_TiO$_2$ (n = 15) | 0.55% | 99.45% |
| 30% (v/v) N_TiO$_2$ (n = 15) | 0.24% | 99.76% |
| 19% (v/v) EtOH (n = 15) | 10.71% | 89.29% |
| 25% (v/v) EtOH (n = 15) | 0.92% | 99.08% |
| 30% (v/v) EtOH (n = 15) | 0.73% | 99.27% |
| 19% (v/v) EtOH + light (n = 15) | 93.79% | 6.21% |
| 25% (v/v) EtOH + light (n = 15) | 7.79% | 92.21% |
| 30% (v/v) EtOH + light (n = 15) | 9.65% | 90.35% |

Table 1: *S. mutans* survival rate and antibacterial efficacy of the groups were investigated. The survival rate (Sr) and Treatment efficacy (Te) were calculated using the following equations: $Sr = (N_f/N_0)100\%$ and $Ae = (N_0 - N_f/N_0)100\%$, where $N_0$ is the initial population and $N_f$ is the viable population after the treatments.

Antibacterial Behavior of N—TiO$_2$ NPs Immobilized in Dental Adhesive Resins

Figure 9:
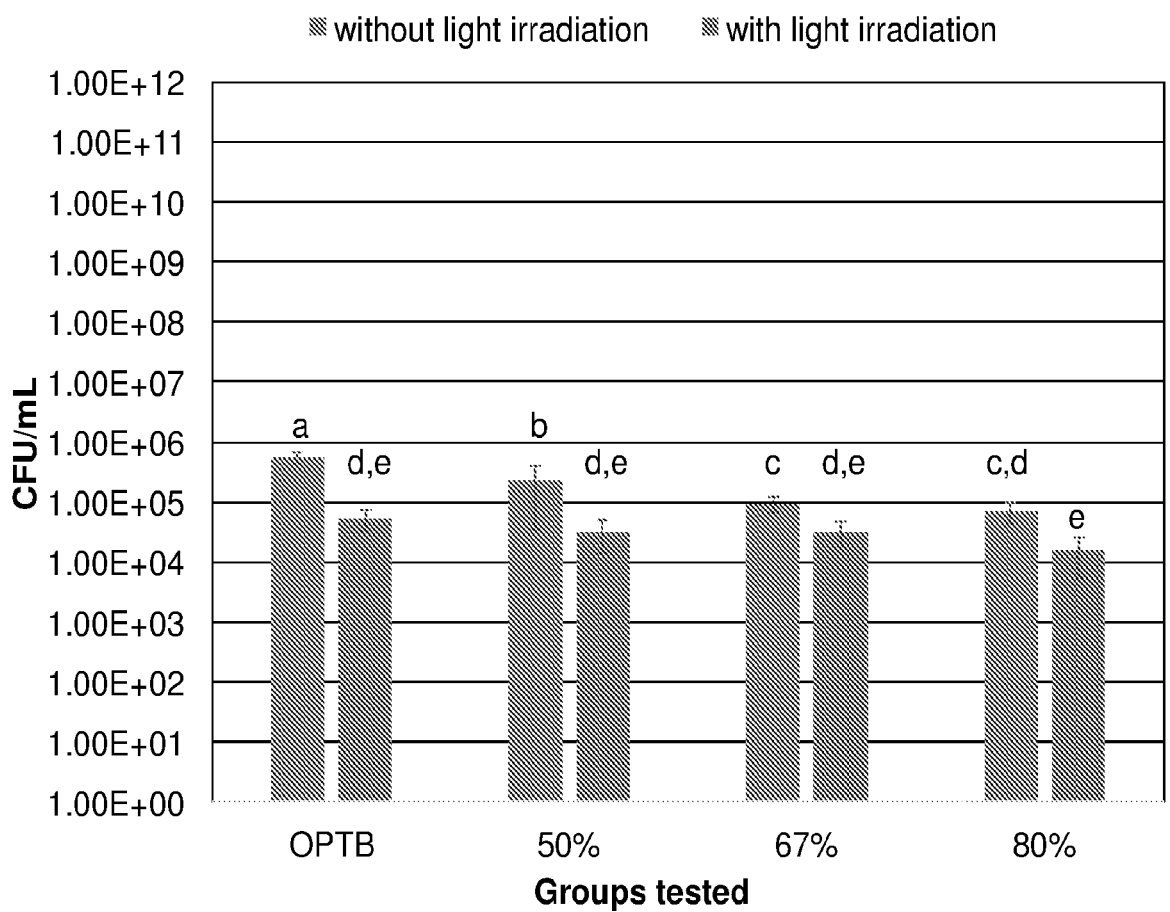
FIG. 9 is a graph showing antibacterial efficacy of control vs. experimental dental adhesive resins containing 50%, 67% and 80% (v/v) of N—$TiO_2$ NPs against 3-hour S. mutans biofilms. Individual columns represent mean and standard deviation values. Lower CFU/mL values indicate groups having higher antibacterial behavior. Distinct letters indicate groups having statistical significant differences according to the SNK post-hoc test.
Figure 10:
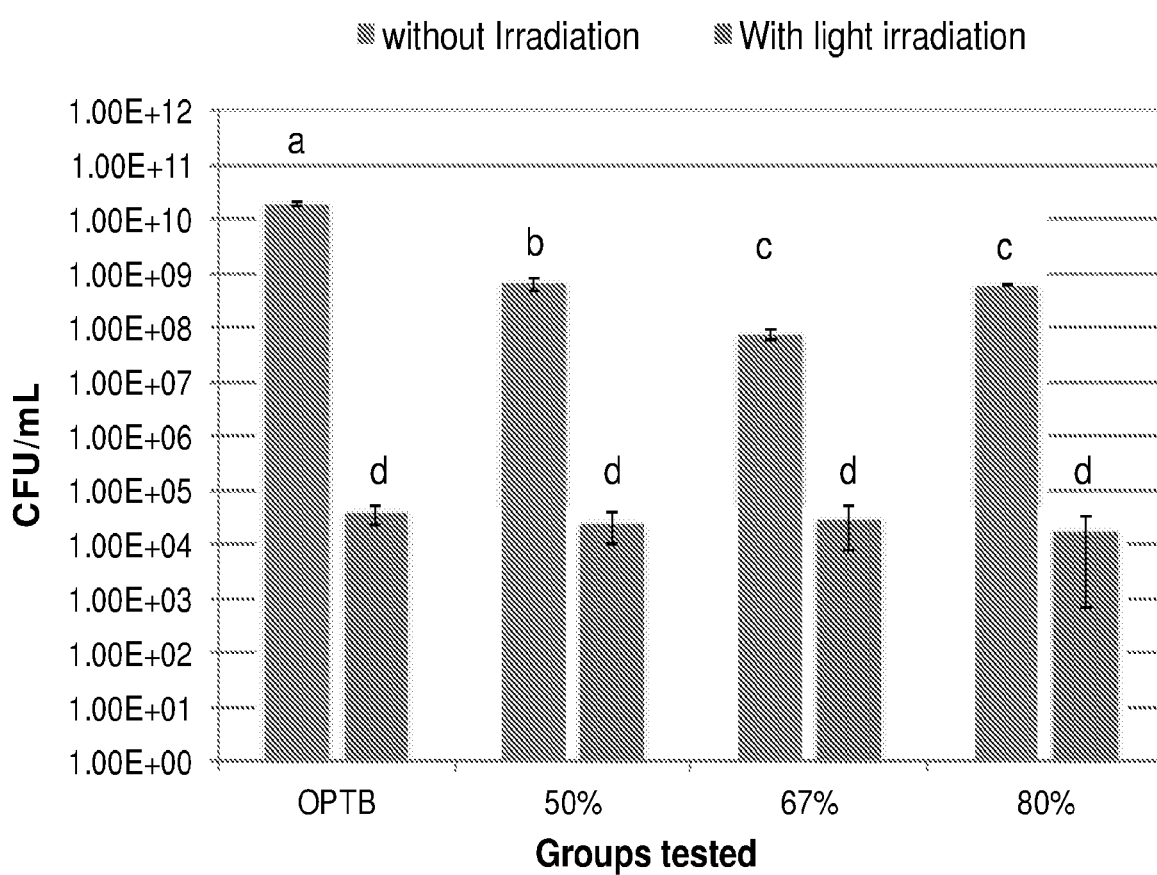
FIG. 10 is a graph showing antibacterial efficacy of control vs. experimental dental adhesive resins containing 50%, 67% and 80% (v/v) of N—$TiO_2$ NPs against 24-hour S. mutans biofilms. Individual columns represent mean and standard deviation values. Lower CFU/mL values indicate groups having higher antibacterial behavior. Distinct letters indicate groups having statistical significant differences according to the SNK post-hoc test.

The results of the antibacterial efficacy of N—TiO$_2$ NPs immobilized in dental adhesive resins against 3- or 24-hour *S. mutans* biofilms grown against the surfaces of specimens of both unaltered and experimental dental adhesive resins under dark or continuous light irradiation conditions were determined using the colony-forming units method (CFU/mL) and are presented as mean and standard deviation values (FIGS. 9 and 10). The results presented indicate, that regardless of the experimental groups tested or periods of time considered (either 3- or 24-hour), biofilms grown under continuous-light irradiation conditions (410±10 nm, 3-hour irradiation=38.75 J/cm$^2$, 24-hour irradiation=310.07 J/cm$^2$) displayed lower viability levels when compared to biofilms pertaining to either the control group or to experimental groups where biofilms were grown without light irradiation. It is also possible to observe that biofilms grown under continuous-light irradiation, displayed similar viability levels independent of the material investigated. In addition, the results of the viability levels of biofilms grown in dark conditions, indicate that experimental adhesive resins have antibacterial properties that are not dependent on light irradiation.

Confocal Laser Scanning Microscopy (CLSM)

Figure 11:
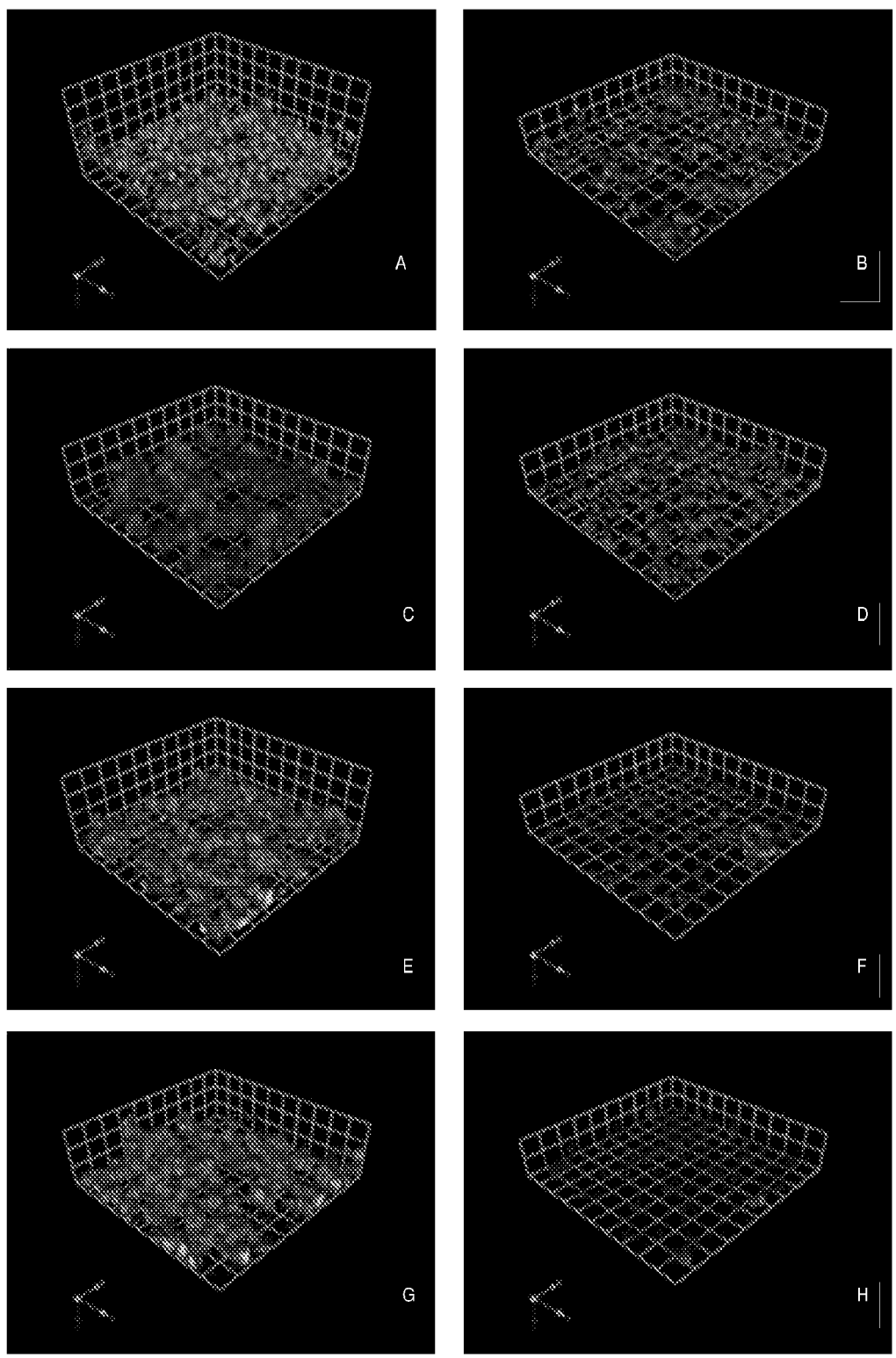
FIG. 11 shows images of results of Confocal laser scanning microscopy (CLSM) analysis. Green and red fluorescence on the images indicate viable and non-viable *S. mutans* colonies, respectively. (A), (C), (E) and (G), represent the results obtained for biofilms grown in dark conditions (24-hours) whereas (B), (D), (F) and (H), represent the results obtained for biofilms grown in continuous light irradiation conditions (24-hours) on both control and experimental dental adhesive resins (50%, 67% and 80% (v/v), respectively).

The CLSM analysis of 24-hour *S. mutans* biofilms grown on the surfaces of both unaltered and experimental dental adhesive resins are presented in FIG. 11. The 3D rendering images revealed that the morphology, biovolume and viability of the cells within the investigated biofilms were significantly altered based on the N—TiO$_2$ NP concentration (50%, 67% and 80% [v/v]) and light irradiation condition (with or without). The results clearly demonstrate that, independent of the experimental group considered, all biofilms grown under continuous-light irradiation conditions (FIGS. 11B, D, F, H) expressed higher instances of red fluorescence, which denotes that these biofilms had lower viability levels than the biofilms grown in dark conditions, which predominantly fluoresced green (FIGS. 11A, C, E, G).

These findings demonstrate that the wavelength and dose of energy used (410±10 nm, 3-hour irradiation=38.75 J/cm$^2$, 24-hour irradiation=310.07 J/cm$^2$) during the biofilms growth significantly impacted the ability of *S. mutans* to sustain viable biofilms. It is also noticeable on the CLSM results (FIGS. 11F and H) that the combination of continuous-light irradiation and experimental materials with higher nanoparticles concentration (67% and 80%) supported biofilms displaying the least amount of biovolume and viability, which can be noted on the images by the presence of extremely sparse micro colonies displaying intense red colors. The results obtained for biofilms pertaining to non-irradiated groups indicate that experimental materials containing 50%, 67% and 80% (v/v) of N—TiO$_2$ NPs in dark conditions displayed antibacterial properties that were not dependent on light irradiation and further confirm the CFU/mL results. This finding can be observed specially in FIGS. 11E and G by the presence of colonies displaying colors that are a mix of red, green and yellow.

In addition, it is also possible to observe, that biofilms grown under dark conditions produced biofilms of similar biovolume and thickness, as noted by the large chained amorphous colonies (FIGS. 11A, C, E, G) regardless of group parameters. This finding indicates that the amounts of dead colonies present on the images are directly proportional to increasing amounts of the N—TiO$_2$ NPs in the materials investigated.

Color Stability

Figure 12:
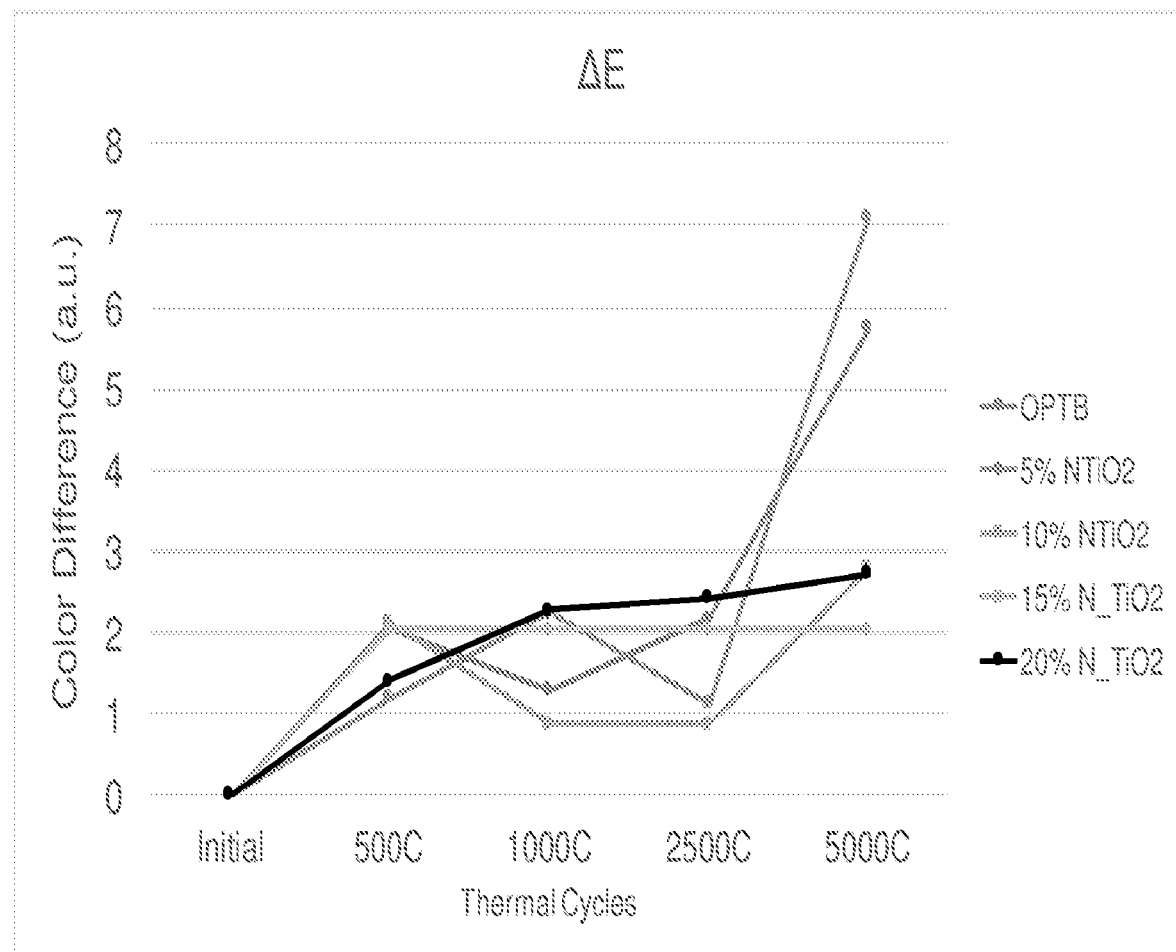
FIG. 12 is a graph showing color stability results in terms of the total color change (ΔE) of dental adhesion specimens containing varying concentrations (5%, 10%, 15%, and 20% (v/v) of N—$TiO_2$ NPs) as compared to a control specimen (OPTB).

The objective of the color analysis was to investigate the effect of the incorporation of 5%, 10%, 15% or 20% (v/v) of N—TiO$_2$ into the dental adhesive resin OPTIBOND SOLO PLUS (OPTB). Disk shaped specimens were fabricated and were subjected to 500, 1000, 2500 and 5000 thermal cycles between two water baths (5° C. and 55° C., dwell time 15 sec.). Digital color analysis was then performed immediately after the fabrication of the specimens and at the completion of each thermal cycle proposed. The color stability of specimens was assessed in terms of total color change (ΔE) using the CIELab color space. The color analysis performed immediately after the fabrication of specimens demonstrated that experimental materials containing varying concentrations of N—TiO$_2$ NPs displayed color changes that were comparable to the unaltered OPTB (FIG. 12). After the completion of 500 thermal cycles it is possible to observe that specimens pertaining to experimental groups containing higher N—TiO$_2$ NPs had the least amount of total color change as compared to OPTB. After the completion of 5000 thermal cycles it became clear that experimental materials containing either 10%, 15% or 20% (v/v) N—TiO$_2$ NPs have displayed the least amount of color variation when compared to OPTB. It is possible to observe that specimens containing 5% (v/v) of N—TiO$_2$ have undergone to color changes that were similar in intensity to the color changes observed in specimens fabricated with the unaltered dental adhesive resin.

These findings indicate that incorporation of N—TiO$_2$ NPs into OPTB rendered materials having improved color stability properties in comparison to the color stability properties of the unaltered and commercially available OPTB. The larger presence of metal oxide nanoparticles with cores resistant to degradation by water and temperature variation could explain the findings regarding the color stability reported in the present research.

Bioactivity of N—TiO$_2$ NPs and N—P—TiO$_2$ NPs

Figure 13:
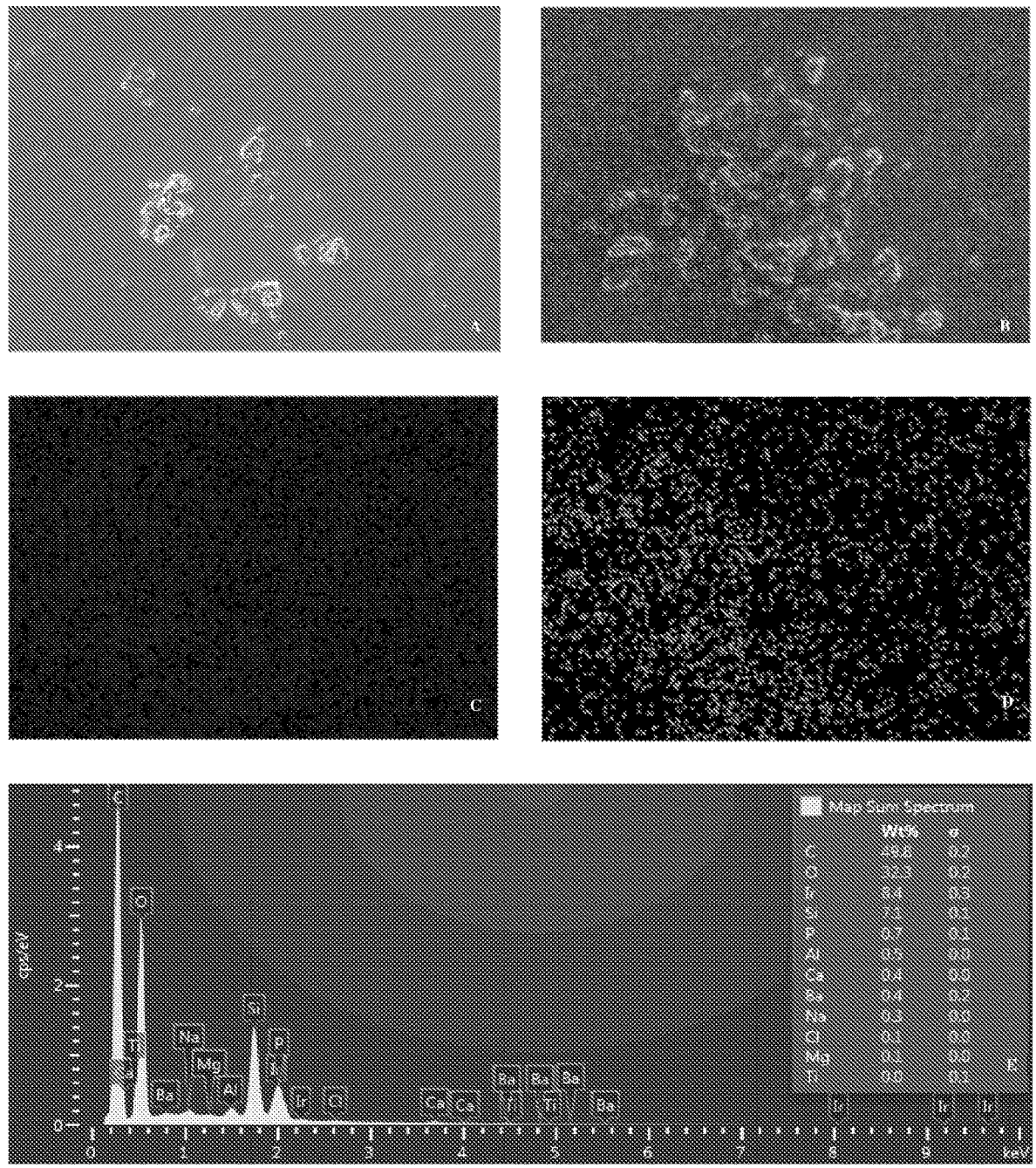
FIG. 13 shows (A) an SEM image (500×) of the surface of a representative control specimen fabricated with OPTB, (B) an EDS layered image (2,000×) demonstrating the distribution of the major elements, (C) EDS Phosphorous mapping (2,000×), (D) Calcium mapping (2,000×), and (E) elemental composition of the specimen determined by EDS.
Figure 14:
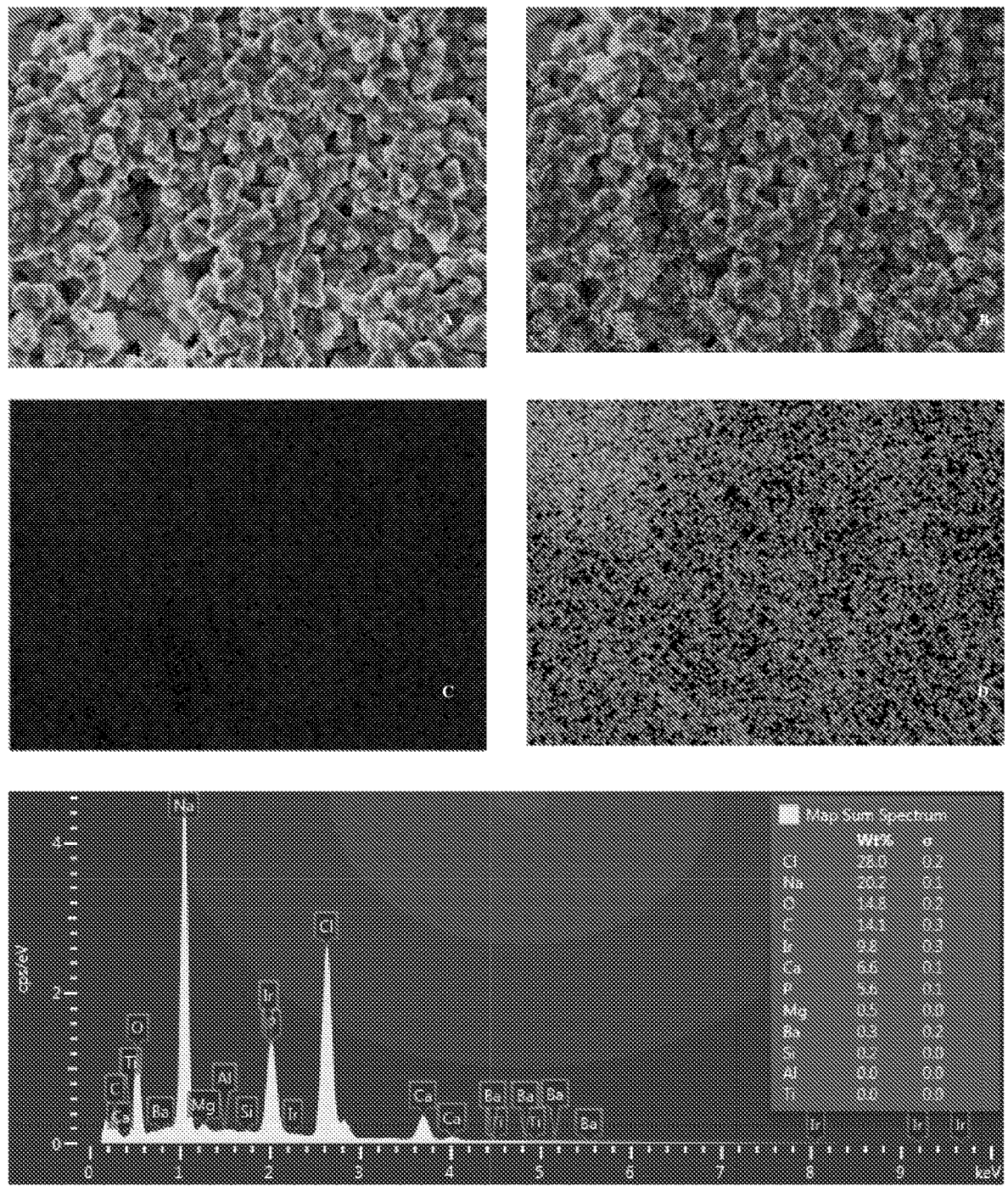
FIG. 14 shows (A) an SEM image (500×) of the surface of a representative specimen fabricated with experimental dental adhesive resin containing 20% (v/v) of N—P—$TiO_2$, (B) an EDS layered image (2,000×) demonstrating the distribution of the major elements, (C) EDS Phosphorous mapping (2,000×), (D) Calcium mapping (2,000×), and (E) elemental composition of the specimen determined by EDS.
Figure 15:
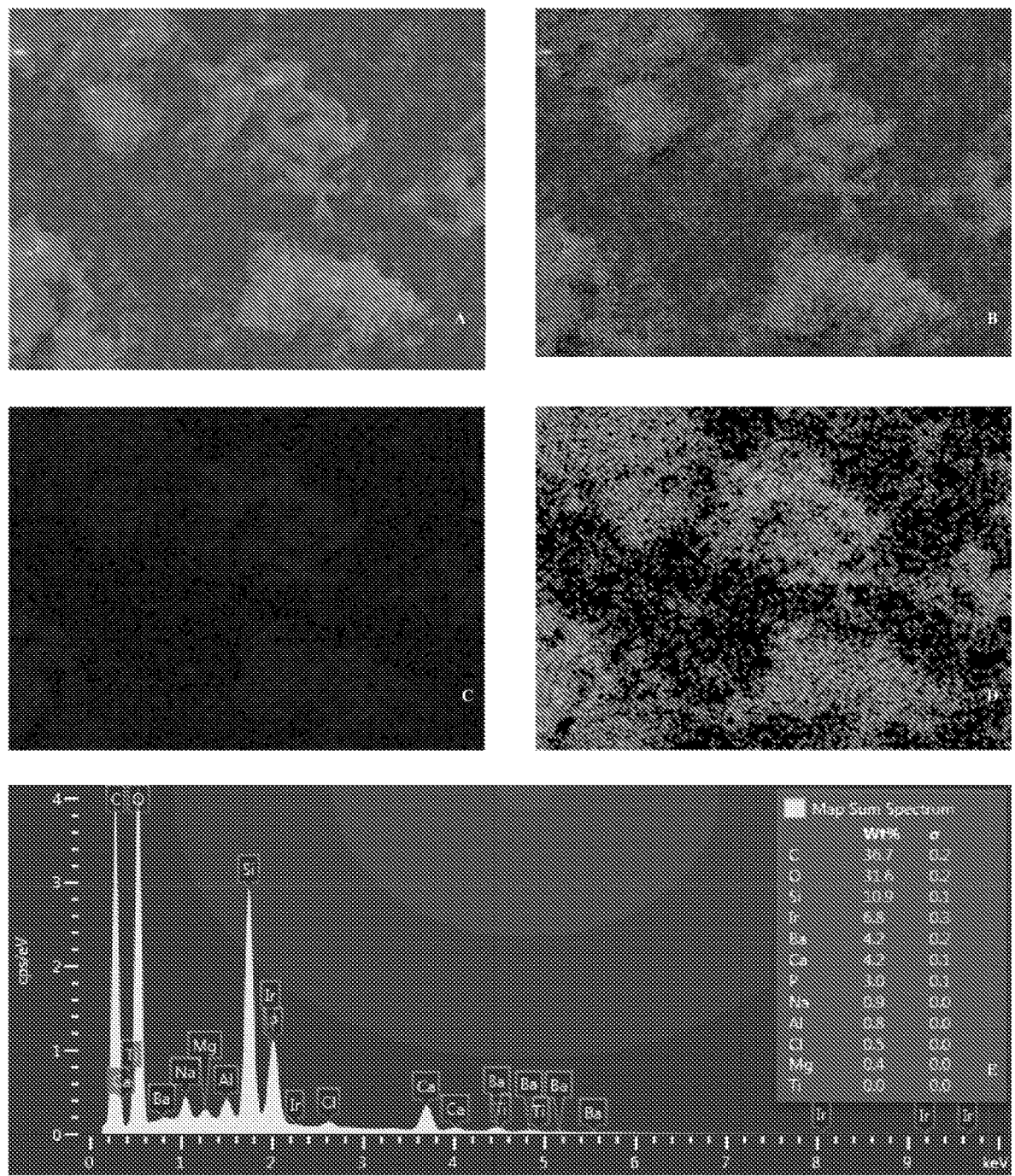
FIG. 15 shows (A) SEM image (500×) of the surface of a representative specimen fabricated with experimental dental adhesive resin containing 20% (v/v) of N—$TiO_2$ NPs, (B) an EDS layered image (2,000×) demonstrating the distribution of the major elements, (C) EDS Phosphorous mapping (2,000×), (D) Calcium mapping (2,000×) and (E) elemental composition of the specimen determined by EDS.

The in vitro testing of the bioactivity of experimental dental adhesive resins containing 20% (v/v) of either N—TiO$_2$ NPs or N—P—TiO$_2$ NPs was conducted to demonstrate the ability of experimental materials to spontaneously deposit a crystalline layer of amorphous calcium phosphate upon exposure to Dulbecco's phosphate buffer solution (DPBS). Specimens fabricated with OPTB-only served as the control group. SEM and EDS analyses were used to characterize the bioactivity of experimental dental adhesive resins. The SEM and EDS representative images presented in FIGS. 13-15 represent the results obtained with the in vitro bioactive testing of unaltered OPTB, as well as with N—P—TiO$_2$ NPs and N—TiO$_2$ NPs, respectively. It is possible to observe from the EDS compositional analysis (FIG. 13E) that specimens fabricated with unaltered OPTB were able to promote the precipitation of very small amounts of calcium (Ca, 0.4%), and phosphorous (P, 0.7%). FIG. 14E represents the EDS compositional analysis results of specimens fabricated with experimental dental adhesive resins containing 20% (v/v) of N—P—$TiO_2$ NPs. It is possible to observe that these materials promoted the highest precipitation of Ca (6.6%) and P (5.6%). FIG. 15E shows the EDS compositional analysis results of specimens fabricated with 20% (v/v) of N—$TiO_2$. The results have demonstrated that these materials promoted an intermediate precipitation of Ca (4.2%) and P (3.0%). In addition, the EDS mapping of individual elements further confirmed the findings of the compositional analysis performed.

Discussion

In at least certain embodiments, doped $TiO_2$ NPs were obtained via a two-step fabrication process. In a first step, undoped $TiO_2$ NPs were synthesized. In a second step, nitrogen-doping, or co-doping of the $TiO_2$ NPs was carried out. After the doping process, the obtained single-doped NPs had their initial visual aspect altered from a bright white— into a yellow—pale suspension, which indicates that the doping process was carried out successfully. The results of the UV-vis spectroscopy of both undoped and N—$TiO_2$ NPs are presented in FIG. 1, which shows that N—$TiO_2$ NPs had higher levels of light absorption when compared to the behavior observed for undoped $TiO_2$ NPs. The nanoparticles had significant absorption behavior in the visible region (between 400 nm and 600 nm).

The SEM analysis of nanoparticles presented in FIG. 2 revealed important aspects related to morphologies and agglomeration levels of nanoparticles. The layered and amorphous structures visible in the images suggest that N—$TiO_2$ NPs have spherical shapes, smooth surfaces and display a strong agglomeration behavior in ethanol (40 mg/mL). The use of surfactants is one approach that could be used to improve the dispersability behavior of N—$TiO_2$ NPs. However, the use of surfactants decreases the possibility of oxidation reactions taking place on the N—$TiO_2$ NP surfaces due to the creation of a physical barrier, thereby diminishing their antibacterial behavior. Thus the methods of the present work were designed to maximize the photocatalytic behavior of N—$TiO_2$ NPs. The SEM images demonstrate a physical association of nanoparticles due to the drying process that is required for SEM imaging.

The results of the compositional characterization of the nanoparticles using EDS are presented in FIG. 3. The analysis revealed that Ti (40.9%), O (39.3%), C (13.3%) and Si (6.5%) were the major components found in N—$TiO_2$ NP samples. However, under the conditions of the present work, the doping element (nitrogen) could not be mapped. Apparently the combination of factors like the low atomic number of nitrogen (Z=7), and the complete overlap between the Ti $L_\lambda$ (0.395 keV) and the N $K_\alpha$ (0.392 KeV) peaks made the mapping of nitrogen in the N—$TiO_2$ NP samples excessively difficult.

Characterization of the NPs by TEM is presented in FIG. 4. The images demonstrated that N—$TiO_2$ NPs have mostly spherical shapes, smooth surfaces and a homogeneous distribution of sizes, with individual NP sizes ranging around 10 nm. It is also possible to observe that N—$TiO_2$ NPs still tend to have strong agglomeration behaviors even for very diluted samples (1:1250 or 0.032 mg/mL). Control over the nanoparticle agglomeration levels is a key factor in the optimization of photocatalytic reactions, because agglomeration can decrease the nanoparticle surface to volume ratio, decrease the amount of free surface area that is actually available for oxidative reactions to take place and, increase the amount of recombination centers present in the bulk of the photocatalyst, thereby adversely impacting the overall photocatalytic behavior of any light responsive material.

SEM and EDS analyses were used to characterize the surface properties and compositions of specimens fabricated with both unaltered and experimental dental adhesive resins. The SEM results demonstrated the successful incorporation of nanoparticles into the polymer matrix, which can be observed by the presence of increasing amounts of particulates on the surfaces of specimens that were fabricated with higher nanoparticles concentrations. In addition, specimens fabricated with higher nanoparticles content displayed rougher surfaces when compared to specimens of OPTB resin due to the strong presence of exposed particulates.

The compositional analysis performed using EDS further corroborates our SEM findings regarding the successful incorporation of nanoparticles into the OPTB. It is possible to observe on the EDS images, that specimens of OPTB displayed barium (Ba), Si, O and C as its major chemical components, which is an expected composition. The compositional mapping of specimens fabricated with experimental dental adhesive resins containing 50%, 67% or 80% (v/v) of N—$TiO_2$ NPs clearly demonstrate higher concentrations of Ti and O, which can be noticed by observing increasing amounts of pink (Ti) and yellow (O) dots on the images. These results agree with the compositions expected for samples fabricated with experimental materials.

The wettability analysis using the measurement of contact angles was made necessary in the present work to investigate the impact of the incorporation of nanoparticles on the wettability characteristics of OPTB. The measurement of contact angles at the solid-liquid-vapor interface is considered to be the most widely known technique used to investigate the wettability of solid surfaces. The hydrophobicity behavior of dental composites is an important factor in the longevity of resin-based materials because it affects the initial absorption of water, which regulates the attachment of oral bacteria. The wettability findings reported in the present work demonstrated that the incorporation of N—$TiO_2$ NPs into OPTB promoted the attainment of experimental materials with wettability properties that were not significantly different when compared to the control group. From the clinical perspective, the fact that there were no statistical differences between the groups is important because in order to promote the establishment of an adequate adhesive layer, dental adhesive resins must compete with water from the dentine substrate to wet the collagen fibrils. Adhesive materials must come into intimate contact with the dentine substrate to allow for the proper micromechanical surface attachment.

When observing results of the assessment of the antibacterial efficacy of N—$TiO_2$ NPs in suspension (FIG. 8 and Table 1), it is possible to see that *S. mutans* biofilms displayed similar CFU/mL values regardless of treatment with either nanoparticles or ethanol. This indicates that the N—$TiO_2$ NPs suspended in 100% ethanol did not present a strong antibacterial effect against *S. mutans* biofilms in the conditions investigated. The analysis of the survival rates (Sr) and treatment efficacy (Te) for the same experimental groups discussed (Table 1) further corroborates this finding.

Oxidative photocatalytic reactions are inhibited in the presence of ethanol because some reactive species of oxygen, such as hydroxyl radicals, are strongly quenched. In the same direction, Hydroxyl radicals and hydrogen peroxide appeared to be the major species associated with the antibacterial effects observed against *Staphylococcus epidermidis*.

Results from antibacterial assays performed herein with experimental adhesive resins containing 50%, 67% or 80% (v/v) of N—$TiO_2$ NPs against *S. mutans* biofilms grown for either 3-hour or 24-h, with or without continuous-light irradiation, are presented in FIGS. 9-10. These results have demonstrated that, independent of growth time (either 3-hour or 24-h), or light irradiation conditions (with or without light), experimental groups containing higher N—$TiO_2$ NP concentrations were more antibacterial in nature when compared to the control group, which indicates the establishment of a concentration-dependent antibacterial mechanism.

The CLSM images presented in FIG. 11 illustrate and further corroborate the results of the antibacterial assays performed on dental adhesive resins. These results confirm a decrease in cells viability and biovolume when specimens were fabricated with higher concentrations of doped $TiO_2$ NPs while also being irradiated with continuous visible light irradiation, and therefore align the expected results with the representative CSLM images. It is interesting to note, that while it was expected that the N—$TiO_2$ NPs would affect the viability of *S. mutans* biofilms when exposed to visible light, it is apparent that there is a toxicity effect ("dark toxicity") absent exposure of the adhesive to light. Although many photosensitizers are able to increase bactericidal effects, they usually require an irradiation light source in order to elicit reduced viability. However, the dark toxicity observed was statistically significant due to decrease in viability between the OPTB control and the 80% N—$TiO_2$ NP adhesive resin in dark conditions in both the 3-hour and 24-hour biofilms. It is also supported by the 24-hour CLSM images that visually show a change in viability, but not necessarily the structure of the biofilm.

Both our CLSM images as well as our CFU/mL results show not only a decrease in biovolume, but also a highly toxic effect when biofilms are grown on an adhesive containing N—$TiO_2$ NPs in the presence of blue light. Since it was previously established that the N—$TiO_2$ NPs do have some degree of dark toxicity, the high degree of bactericidal effects may have been due to a two-fold mechanism; the restriction of EPS in the formation of the biofilm, as well as the toxicity of the nanoparticles themselves.

In the present work, a titanium dioxide-based photocatalyst was successfully prepared by doping $TiO_2$ NPs with nitrogen using a simple solvothermal method. These NPs were demonstrated to have superior visible light absorption levels when compared to pure $TiO_2$ NPs due to the contribution of substitutional nitrogen in the crystal lattice of titania. The visible light-driven antibacterial efficacy of N—$TiO_2$ NPs was investigated for nanoparticles suspended in ethanol and incorporated in a commercially available dental adhesive resin (OPTB). It was demonstrated that nanoparticles in suspension have only a limited antibacterial behavior against *S. mutans* biofilms probably due to the use of ethanol as a solvent, which is a well-known potent hydroxyl scavenger. The present work has shown for the first time that specimens fabricated with experimental dental adhesive resins containing either 50%, 67% or 80% (v/v) of N—$TiO_2$ NPs were shown to have strong antibacterial behavior in both, dark and light irradiated conditions, when compared to the antibacterial behavior of unaltered dental adhesive resins (e.g., OPTB). This indicates that N—$TiO_2$ NPs comprise a feasible antibacterial agent against oral cariogenic biofilms. The present work has also demonstrated that experimental materials had similar wettability behaviors when compared to the unaltered adhesive resins, which is important from the clinical perspective.

Example 2

Polymerization shrinkage, poor adhesive infiltration and incomplete enveloping of dentin matrix are important limitations of current dental adhesive resins. The approach of this example to solving these problems was the development of a bioactive and bond-promoting adhesive resin containing N—$TiO_2$ NPs. The spontaneous and light-stimulated deposition of hydroxyapatite on the surfaces of specimens fabricated with both experimental [20% (v/v) N—$TiO_2$ NPs] and unaltered dental adhesive resin (OPTB) was investigated. Experimental resins were synthesized by adding 20% (v/v) N—$TiO_2$ NPs (Oak Ridge National Laboratory) to OPTB. Thin-films (n=12/group; d=12 mm, t=15 μm) were fabricated and light-cured (40 sec, 457±15 nm) on acid-etched glass cover slips in preparation for bioactivity testing. Thin-films were then irradiated (405±15 nm) for 1, 3, and 8 hours either in air or water (2.5 mL) conditions. Specimens were then immersed in pre-heated DPBS (Dubelcco's Phosphate-Buffered Saline, with Calcium and Magnesium Chloride) aqueous solution (40 mL/specimen, 60° C.) and were stored in dark conditions (37° C.) for 7 days. Solutions of DPBS were subsequently replenished at 72-h and 120-h. Specimens were air dried in dark conditions (minimum of 24-h) and were sputter-coated with either iridium or gold in preparation for Scanning Electron Microscopy and Energy Dispersive X-ray Spectroscopy analyses. Chemical compositional data provided by EDS was analyzed using GLM and SNK post hoc tests ($\alpha=0.05$).

Mean deposition values of calcium and phosphorous ranged from 0.60 and 1.13 wt % [Control, irradiated (1 h) in water] to 6.73 and 6.13 wt % [20% (v/v) N—$TiO_2$ NPs, irradiated (8 h) in air], respectively. Significant differences were found in the interaction "material*irradiation time*irradiation condition" ($p<0.05$). It was concluded that experimental dental adhesive resins containing 20% (v/v) of N—$TiO_2$ NPs that were irradiated for 8 h in air conditions, were demonstrated to have bioactive properties that were stimulated by visible light irradiation, as hypothesized.

Example 3

Caries is the primary reason of dental restoration failure. The objective of this example was to assess the wettability, color stability and fracture toughness of adhesives containing N—$TiO_2$ NPs.

Experimental adhesives were synthesized by adding 5%, 10%, 15% and 20% (v/v) of N—$TiO_2$ NPs to OPTB. Unaltered adhesive resin (OPTB) served as the control group. Dentin specimens (a=5 $mm^2$, t=1 mm) were fabricated to test wettability. Disk-shaped (d=7.64 mm, t=1.75 mm) and SENB (17.6×2.0×4.0 mm) specimens were fabricated for wettability and fracture toughness testing. Wettability of adhesives was tested in an OCA15-Plus goniometer. Profiles of adhesive drops were analyzed (25 frames/s, 37° C.) to determine contact angle at time=0 s ($\theta_{INITIAL}$) and time=30 s ($\theta_{FINAL}$). Color stability (n=5/concentration) was tested using an image analysis software after 0, 500, 1,000, 2,500 and 5,000 thermal cycles (5° C.-55° C., 15 s dwell). Fracture toughness specimens were tested with an Instron system using ASTM Standard D5045-99. Data was analyzed using GLM and SNK post hoc tests ($\alpha=0.05$).

Mean $\theta_{INITIAL}$ values ranged from 95.87° (Control) to 49.69° (20% N—TiO$_2$ NPs) and for $\theta_{FINAL}$ from 30.98° (5% N—TiO$_2$) to 25.00° (20% N—TiO$_2$ NPs). Mean L*, a* and b* values ranged from 79.93, −5.06 and 3.65 (5% N—TiO$_2$) to 84.51, −4.50 and 4.33 (15% N—TiO$_2$ NPs), respectively. No significant differences (p>0.05) were observed for initial or final wettability. Significant differences among groups were found for color stability (p<0.0001). Mean $K_{1c}$ values ranged from 0.431 MPa (20% N—TiO$_2$ NPs) to 4.317 MPa (5% N—TiO$_2$ NPs), but results were rejected because they couldn't be validated using Standard D5045-99. It was concluded that adhesive resins containing N—TiO$_2$ NPs had comparable wettability and better color stability than unaltered adhesive resin (control), as hypothesized.

Example 4

The antibacterial efficacy of unaltered and experimental (doped) dental adhesive resins against non-disrupted cariogenic (caries producing) biofilms was further assessed in terms of relative luminescence units (RLUs) using a real-time luciferase-based bioluminescence assay. Toward this end, experimental dental adhesive resins containing either N—TiO$_2$ NPs (5%-30%, v/v), N—F—TiO$_2$ NPs (30%, v/v) and N—Ag—TiO$_2$ NPs (30%, v/v) were synthesized by dispersing the nanoparticles in OBSP adhesive resin using a sonicator (4 cycles of 1 min, intervals of 15-sec between cycles; Q700, QSonica, USA). Two non-antibacterial (OBSP, and Scotchbond Multipurpose, 3M ESPE, USA) and one antibacterial (Clearfil SE Protect, Kuraray, Noritake Dental Inc., Japan) commercially available dental adhesive resins were also tested for antibacterial functionalities. *Streptococcus mutans* biofilms were grown (UA159-ldh, JM 10; 37° C., microaerophilic) on the surfaces of disk-shaped specimens (n=18/group, d=6.0 mm, t=0.5 mm) for either 24 or 48 hours with or without continuous visible light irradiation (405±15 nm). One set of specimens was fabricated with OBSP and was treated with Chlorhexidine 2% (2 min) that served as our control group. Results for the antibacterial efficacies of both unaltered and experimental dental adhesive resins containing either doped or co-doped TiO$_2$ NPs under continuous visible light irradiation for either 24 or 48 hours, demonstrated that all groups tested displayed similar antibacterial behaviors under continuous visible light irradiation. Such findings suggest that under the conditions investigated (wavelength and power intensity), visible light irradiation had a very strong antibacterial behavior that took place independently of the antibacterial activity of the substrate where biofilms were grown (either antibacterial or not). Such impact made impossible the determination of the materials' real antibacterial efficacies under such light irradiation conditions.

Experiments were then conducted under dark conditions; bacteria were grown in dark conditions for either 24 and 48 hours. The results indicated that the TiO$_2$-containing adhesive resins were more antibacterial than commercially available non-antibacterial dental adhesive resins (such as Opti-Bond Solo Plus and Scotchbond Multipurpose). The experimental dental adhesive resins containing 30% (v/v) of nanoparticles (N—TiO$_2$ NPs, N—F—TiO$_2$ NPs and N—Ag—TiO$_2$ NPs) displayed antibacterial efficacies in dark conditions that were similar to Clearfil SE Protect (Fluoride-releasing material, Kuraray, Noritake Dental Inc., Japan). *S. mutans* biofilms grown on specimens treated with chlorhexidine 2% (2 min) displayed the lowest RLU values amongst all groups investigated, thereby confirming the strong antibacterial behavior of non-immobilized chlorhexidine. In addition, the antibacterial effect was demonstrated to be concentration-dependent, wherein experimental adhesive resins containing higher concentrations of antibacterial nanoparticles (either doped or co-doped) displayed stronger antibacterial effects against non-disrupted *S. mutans* biofilms. Since long intra-oral irradiation periods (24-hour and 48-hour) are impractical and clinically not feasible, associated with the fact that these materials are intended to be used in the oral cavity's dark conditions, these results were considered of paramount importance and clinically relevant for the commercialization pathway of recently developed antibacterial and bioactive nano-filled dental adhesive resins.

Optical and mechanical properties of both unaltered and experimental dental adhesive resins containing 5%-30% (v/v, 5% increments) of N—TiO$_2$ NPs were assessed in terms of color stability and biaxial flexure strength. Color stability (n=5) and biaxial flexure strength (n=8) specimens (d=6.0 mm, t=0.5 mm) were fabricated and tested using a color analysis software (ScanWhite, Darwin Syst., Brazil) and an Instron universal testing machine (cross-head rate=1.27 mm/min), respectively. Color stability measurements were performed immediately after specimen fabrication and after water storage (1, 2, 3, 4, 5, 6 months; 37° C.). The color stability results demonstrated that specimens fabricated using either unaltered or experimental dental adhesive resins containing N—TiO$_2$ NPs (5%-30%, v/v) were subjected to color changes induced by long-term water storage. The highest color variations were observed at two months of water storage (37° C.) for specimens pertaining to experimental groups containing either 5% or 10% of N—TiO$_2$ NPs. Specimens fabricated with unaltered Opti-Bond Solo Plus have demonstrated color variations that were similar to the color variations observed for the experimental group containing 20% N—TiO$_2$ NPs. Specimens fabricated with 30% N—TiO$_2$ NP-containing dental adhesive resins have shown the least amount of color variation throughout the investigation time (6-mo), and therefore, were considered as the most color stable amongst all materials investigated. From the esthetic standpoint, the human eye can only detect differences in color above a certain threshold ($\Delta E \geq 3$).

In at least one embodiment, dental composition specimens fabricated with at 30% N—TiO$_2$ NPs displayed color variations that were either lower than or close to the human eye detection capability, thereby corroborating the long-term use of these highly esthetic experimental dental adhesive resins. In at least certain embodiments, the dental compositions contain at least 5% to 80% (v/v) of doped-TiO$_2$ NPs as disclosed herein, such as at least 5% (v/v), at least 6% (v/v), at least 7% (v/v), at least 8% (v/v), at least 9% (v/v), at least 10% (v/v), at least 11% (v/v), at least 12% (v/v), at least 13% (v/v), at least 14% (v/v), at least 15% (v/v), at least 16% (v/v), at least 17% (v/v), at least 18% (v/v), at least 19% (v/v), at least 20% (v/v), at least 21% (v/v), at least 22% (v/v), at least 23% (v/v), at least 24% (v/v), at least 25% (v/v), at least 26% (v/v), at least 27% (v/v), at least 28% (v/v), at least 29% (v/v), at least 30% (v/v), at least 31% (v/v), at least 32% (v/v), at least 33% (v/v), at least 34% (v/v), at least 35% (v/v), at least 36% (v/v), at least 37% (v/v), at least 38% (v/v), at least 39% (v/v), at least 40% (v/v), at least 41% (v/v), at least 42% (v/v), at least 43% (v/v), at least 44% (v/v), at least 45% (v/v), at least 46% (v/v), at least 47% (v/v), at least 48% (v/v), at least 49% (v/v), at least 50% (v/v), at least 51% (v/v), at least 52% (v/v), at least 53% (v/v), at least 54% (v/v), at least 55% (v/v), at least 56% (v/v), at least 57% (v/v), at least 58%

(v/v), at least 59% (v/v), at least 60% (v/v), at least 61% (v/v), at least 62% (v/v), at least 63% (v/v), at least 64% (v/v), at least 65% (v/v), at least 66% (v/v), at least 67% (v/v), at least 68% (v/v), at least 69% (v/v), at least 70% (v/v), at least 71% (v/v), at least 72% (v/v), at least 73% (v/v), at least 74% (v/v), at least 75% (v/v), at least 76% (v/v), at least 77% (v/v), at least 78% (v/v), at least 79% (v/v), or at least 80% (v/v), with the balance comprising the curable adhesive resin material, and optionally other components as described elsewhere herein.

The present results demonstrate that experimental dental adhesive resins containing varying concentrations of N—$TiO_2$ NPs display biaxial flexure strengths that are either similar or better than the strength observed for specimens fabricated with the unaltered OBSP. No differences were observed among the flexure strengths of experimental groups, thereby indicating that the presently disclosed materials can behave very similar to commercially available materials when subjected to masticatory forces.

Specimens (d=6.0 mm, t=0.5 mm) of the unaltered resins and experimental dental adhesive resins containing 30% N—$TiO_2$ NPs, 30% N—F—$TiO_2$ NPs and 30% N—Ag—$TiO_2$ NPs were fabricated and characterized using the state of the art scanning electron microscope. This dual focused ion-beam microscope (Dual-FIB SEM/EDS) is capable, through a destructive process, to characterize and map the chemical composition and distribution of elements in three dimensions. The 3-D characterization and localization of components clearly demonstrated that experimental materials containing co-doped nanoparticles (e.g., 30% v/v, N—F—$TiO_2$ NPs) displayed an optimized dispersion of filler particles (part of the original composition) when compared to the filler particle distribution observed on specimens fabricated with the unaltered dental adhesive resin. The 3-D images demonstrated that the experimental adhesive resins had more filler particles per unit volume with a more homogeneous size distribution than the filler fraction and size distribution observed on OptiBond Solo Plus samples. In addition, results showed that larger and more agglomerated filler particles tend to result in a polymer matrix containing more pores per unit volume. This finding was corroborated by the pore-size distribution calculated for the unaltered samples and experimental dental adhesive resin samples, where it is possible to observe that the quantity and sizes of pores formed in experimental materials were smaller when compared to the unaltered OptiBond Solo Plus samples.

In at least one embodiment, the present disclosure includes a dental composition, comprising doped and/or coated $TiO_2$ NPs, and a curable resin material, wherein the curable resin material comprises a polymer precursor component. The $TiO_2$ NPs may comprise at least one dopant or coating selected from the group consisting of N (nitrogen), Ag (silver), F (fluorine), P (phosphorus), and $PO_4$ (phosphate). As noted above, in non-limiting embodiments, the dental composition may comprise a volume to volume ratio of doped $TiO_2$ NPs to curable resin material in a range of 1% to 80% (v/v), 5% to 50% (v/v), or 10% to 40% (v/v), for example. The polymer precursor component may be photocurable. The polymer precursor may be selected from the group consisting of acrylates, methacrylates, dimethacrylates, epoxies, vinyls and thiols. The polymer precursor may be selected from the group consisting of ethylenedimethacrylate ("EDMA"), bisphenol A glycidyl methacrylate ("BisGMA"), triethyleneglycol dimethacrylate ("TEGDMA"), 1,6-bis(methacryloxy-2-ethoxycarbonylamino)-2,4,4-trimethylhexane (UDMA), pyromellitic glycerol dimethacrylate (PMGDM), and 2-hydroxyethyl methacrylate (HEMA). The dental composition may comprise at least one solvent. The at least one solvent may be selected from the group consisting of water, ethanol, methanol, toluene, ethyl ether, cyclohexane, isopropanol, chloroform, ethyl acetate, acetone, hexane, and heptanes. The dental composition may comprise a polymerization initiator. The dental composition may comprise a filler. The dental composition may be selected from the group consisting of dental resins, dental bonding agents, dental adhesives, dental cements, dental restoratives, dentals coatings, dental sealants, acrylic resins, and denture teeth. The dental composition may comprise bioactive and/or antibacterial activity in the absence of visible or ultraviolet light. The dental composition may be used to form a hardened dental article after a photocuring step. In at least one embodiment, the disclosure includes an in vivo dental process, comprising applying the dental composition to at least one of a dental restorative and a dental substrate, and causing the dental restorative to be bonded to the dental substrate via the dental composition after a step of photocuring the dental composition.

Accordingly, the present disclosure is directed to at least the following non-limiting embodiments:

Clause 1. In at least one embodiment the present disclosure includes a dental composition, comprising doped $TiO_2$ nanoparticles, and a curable resin material, wherein the curable resin material comprises a polymer precursor component.

Clause 2. The dental composition of clause 1, wherein the doped $TiO_2$ nanoparticles comprise at least one dopant selected from the group consisting of N (nitrogen), Ag (silver), F (fluorine), P (phosphorus), and $PO_4$ (phosphate).

Clause 3. The dental composition of clause 1 or 2, wherein the doped $TiO_2$ nanoparticles further comprise at least one second dopant selected from the group consisting of N, Ag, F, P, and $PO_4$.

Clause 4. The dental composition of any one of clauses 1-3, comprising a volume to volume ratio of doped $TiO_2$ nanoparticles to curable resin material in a range of 1% to 80% (v/v).

Clause 5. The dental composition of any one of clauses 1-4, comprising a volume to volume ratio of doped $TiO_2$ nanoparticles to curable resin material in a range of 5% to 50% (v/v).

Clause 6. The dental composition of any one of clauses 1-5, comprising a volume to volume ratio of doped $TiO_2$ nanoparticles to curable resin material in a range of 10% to 40% (v/v).

Clause 7. The dental composition of any one of clauses 1-6, wherein the polymer precursor component is photocurable.

Clause 8. The dental composition of any one of clauses 1-7, wherein the polymer precursor is selected from the group consisting of acrylates, methacrylates, dimethacrylates, epoxies, vinyls and thiols.

Clause 9. The dental composition of any one of clauses 1-8, wherein the polymer precursor is at least one selected from the group consisting of ethylenedimethacrylate (EDMA), bisphenol A glycidyl methacrylate (BisGMA), triethyleneglycol dimethacrylate (TEGDMA), 1,6-bis(methacryloxy-2-ethoxycarbonylamino)-2,4,4-trimethylhexane (UDMA), pyromellitic glycerol dimethacrylate (PMGDM), and 2-hydroxyethyl methacrylate (HEMA).

Clause 10. The dental composition of any one of clauses 1-9, further comprising at least one solvent.

Clause 11. The dental composition of any one of clauses 1-10, further comprising a solvent selected from the group consisting of water, ethanol, methanol, acetone, toluene, ethyl ether, cyclohexane, isopropanol, chloroform, ethyl acetate, hexane, and heptanes.

Clause 12. The dental composition of any one of clauses 1-11, further comprising a polymerization initiator.

Clause 13. The dental composition of any one of clauses 1-12, further comprising a filler.

Clause 14. The dental composition of any one of clauses 1-13, wherein the curable resin material is selected from the group consisting of dental resins, dental bonding agents, dental adhesives, dental cements, dental restoratives, dentals coatings, dental sealants, acrylic resins, and denture teeth.

Clause 15. The dental composition of any one of clauses 1-14, comprising bioactive and/or antibacterial activity in the absence of visible or ultraviolet light.

Clause 16. A kit for forming a dental composition, the kit comprising doped $TiO_2$ nanoparticles, and a curable resin material, wherein the curable resin material comprises a polymer precursor component.

Clause 17. The kit of clause 16, wherein the doped $TiO_2$ nanoparticles comprise at least one dopant selected from the group consisting of N (nitrogen), Ag (silver), F (fluorine), P (phosphorus), and $PO_4$ (phosphate).

Clause 18. The kit of clause 16 or 17, wherein the doped $TiO_2$ nanoparticles further comprise at least one second dopant selected from the group consisting of N, Ag, F, P, and $PO_4$.

Clause 19. The kit of any one of clauses 16-18, comprising sufficient doped $TiO_2$ nanoparticles and curable resin material such that the dental composition comprises a volume to volume ratio of doped $TiO_2$ nanoparticles to curable resin material in a range of 1% to 80% (v/v).

Clause 20. The kit of any one of clauses 16-19, comprising sufficient doped $TiO_2$ nanoparticles and curable resin material such that the dental composition comprises a volume to volume ratio of doped $TiO_2$ nanoparticles to curable resin material in a range of 5% to 50% (v/v).

Clause 21. The kit of any one of clauses 16-20, comprising sufficient doped $TiO_2$ nanoparticles and curable resin material such that the dental composition comprises a volume to volume ratio of doped $TiO_2$ nanoparticles to curable resin material in a range of 10% to 40% (v/v).

Clause 22. The kit of any one of clauses 16-21, wherein the polymer precursor component is photocurable.

Clause 23. The kit of any one of clauses 16-22, wherein the polymer precursor is selected from the group consisting of acrylates, methacrylates, dimethacrylates, epoxies, vinyls and thiols.

Clause 24. The kit of any one of clauses 16-23, wherein the polymer precursor is at least one selected from the group consisting of ethylenedimethacrylate (EDMA), bisphenol A glycidyl methacrylate (BisGMA), triethyleneglycol dimethacrylate (TEGDMA), 1,6-bis(methacryloxy-2-ethoxycarbonylamino)-2,4,4-trimethylhexane (UDMA), pyromellitic glycerol dimethacrylate (PMGDM), and 2-hydroxyethyl methacrylate (HEMA).

Clause 25. The kit of any one of clauses 16-24, further comprising at least one solvent.

Clause 26. The kit of any one of clauses 16-25, further comprising a solvent selected from the group consisting of water, ethanol, methanol, acetone, toluene, ethyl ether, cyclohexane, isopropanol, chloroform, ethyl acetate, hexane, and heptanes.

Clause 27. The kit of any one of clauses 16-26, further comprising a polymerization initiator for combining with the doped $TiO_2$ nanoparticles, and curable resin material.

Clause 28. The kit of any one of clauses 16-27, further comprising a filler for combining with the doped $TiO_2$ nanoparticles, and curable resin material.

Clause 29. The kit of any one of clauses 16-28, wherein the curable resin material is selected from the group consisting of dental resins, dental bonding agents, dental adhesives, dental cements, dental restoratives, dentals coatings, dental sealants, acrylic resins, and denture teeth.

Clause 30. The kit of any one of clauses 16-29, wherein the dental composition has bioactive and/or antibacterial activity in the absence of visible or ultraviolet light.

Clause 31. A hardened dental article formed from the dental composition of any one of clauses 1-15, after the dental composition has been photocured.

Clause 32. An in vivo dental process, comprising: applying a dental composition to a dental surface, the dental composition comprising doped $TiO_2$ nanoparticles, and a curable resin material, wherein the curable resin material comprises a polymer precursor component; and causing the dental composition to be bonded to the dental surface by photocuring the dental composition.

Clause 33. The dental process of clause 32, wherein the dental surface is at least one of a dental restorative and a dental substrate.

Clause 34. The dental process of clause 32 or 33, wherein the doped $TiO_2$ nanoparticles comprise at least one dopant selected from the group consisting of N (nitrogen), Ag (silver), F (fluorine), P (phosphorus), and $PO_4$ (phosphate).

Clause 35. The dental process of any one of clauses 32-34, wherein the doped $TiO_2$ nanoparticles further comprise at least one second dopant selected from the group consisting of N, Ag, F, P, and $PO_4$.

Clause 36. The dental process of any one of clauses 32-35, wherein the dental composition comprises a volume to volume ratio of doped $TiO_2$ nanoparticles to curable resin material in a range of 1% to 80% (v/v).

Clause 37. The dental process of any one of clauses 32-36, wherein the dental composition comprises a volume to volume ratio of doped $TiO_2$ nanoparticles to curable resin material in a range of 5% to 50% (v/v).

Clause 38. The dental process of any one of clauses 32-37, wherein the dental composition comprises a volume to volume ratio of doped $TiO_2$ nanoparticles to curable resin material in a range of 10% to 40% (v/v).

Clause 39. The dental process of any one of clauses 32-38, wherein the polymer precursor component is photocurable.

Clause 40. The dental process of any one of clauses 32-39, wherein the polymer precursor is selected from the group consisting of acrylates, methacrylates, dimethacrylates, epoxies, vinyls and thiols.

Clause 41. The dental process of any one of clauses 32-40, wherein the polymer precursor is at least one selected from the group consisting of ethylenedimethacrylate (EDMA), bisphenol A glycidyl methacrylate (BisGMA), triethyleneglycol dimethacrylate (TEGDMA), 1,6-bis(methacryloxy-2-ethoxycarbonylamino)-2,4,4-trimethylhexane (UDMA), pyromellitic glycerol dimethacrylate (PMGDM), and 2-hydroxyethyl methacrylate (HEMA).

Clause 42. The dental process of any one of clauses 32-41, wherein the dental composition further comprises at least one solvent.

Clause 43. The dental process of any one of clauses 32-42, further comprising a solvent selected from the group consisting of water, ethanol, methanol, acetone, toluene, ethyl ether, cyclohexane, isopropanol, chloroform, ethyl acetate, hexane, and heptanes.

Clause 44. The dental process of any one of clauses 32-43, wherein the dental composition further comprises a polymerization initiator.

Clause 45. The dental process of any one of clauses 32-44, wherein the dental composition further comprises a filler.

Clause 46. The dental process of any one of clauses 32-45, wherein the curable resin material is selected from the group consisting of dental resins, dental bonding agents, dental adhesives, dental cements, dental restoratives, dentals coatings, dental sealants, acrylic resins, and denture teeth.

Clause 47. The dental process of any one of clauses 32-46, wherein after curing, the dental composition has bioactive and/or antibacterial activity in the absence of visible or ultraviolet light.

Clause 48. The dental process of any one of clauses 32-47, wherein the dental surface has been acid-etched prior to the application of the dental composition thereon.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims.

What is claimed is:

1. A dental composition, comprising nitrogen-doped $TiO_2$ nanoparticles (NPs), and a curable resin material, wherein (1) the nitrogen-doped $TiO_2$ NPs are produced using a solvothermal process, (2) the curable resin material comprises a polymer precursor component, and (3) the nitrogen-doped $TiO_2$ NPs have antibacterial activity without irradiation by visible or ultraviolet light.

2. The dental composition of claim 1, wherein the nitrogen-doped $TiO_2$ NPs further comprise one or more dopants selected from the group consisting of Ag (silver), F (fluorine), P (phosphorus), and $PO_4$ (phosphate).

3. The dental composition of claim 1, comprising a volume to volume ratio of nitrogen-doped $TiO_2$ NPs to curable resin material in a range of 1% to 80% (v/v).

4. The dental composition of claim 1, wherein the polymer precursor component is photocurable.

5. The dental composition of claim 1, wherein the polymer precursor is selected from the group consisting of acrylates, methacrylates, dimethacrylates, epoxies, vinyls and thiols.

6. The dental composition of claim 1, wherein the polymer precursor is at least one selected from the group consisting of ethylenedimethacrylate (EDMA), bisphenol A glycidyl methacrylate (BisGMA), triethyleneglycol dimethacrylate (TEGDMA), 1,6-bis(methacryloxy-2-ethoxycarbonylamino)-2,4,4-trimethylhexane (UDMA), pyromellitic glycerol dimethacrylate (PMGDM), and 2-hydroxyethyl methacrylate (HEMA).

7. The dental composition of claim 1, further comprising at least one solvent.

8. The dental composition of claim 7, wherein the at least one solvent is selected from the group consisting of water, ethanol, methanol, acetone, toluene, ethyl ether, cyclohexane, isopropanol, chloroform, ethyl acetate, hexane, and heptanes.

9. The dental composition of claim 1, further comprising a polymerization initiator.

10. The dental composition of claim 1, further comprising a filler.

11. The dental composition of claim 1, wherein the curable resin material is selected from the group consisting of dental resins, dental bonding agents, dental adhesives, dental cements, dental restoratives, dentals coatings, dental sealants, acrylic resins, and denture teeth.

12. The dental composition of claim 1, wherein the nitrogen-doped $TiO_2$ NPs have a N/Ti ratio of about 3.4.

13. The dental composition of claim 1, comprising a volume to volume ratio of nitrogen-doped $TiO_2$ NPs to curable resin material in a range of 10% to 40% (v/v).

14. A method of treating a dental surface, comprising:
    applying to the dental surface a dental composition comprising nitrogen-doped $TiO_2$ nanoparticles (NPs) and a curable resin material, wherein (1) the nitrogen-doped $TiO_2$ NPs are produced using a solvothermal process, (2) the curable resin material comprises a polymer precursor component, and (3) the nitrogen-doped $TiO_2$ NPs have antibacterial activity without irradiation by visible or ultraviolet light; and
    bonding the dental composition to the dental surface by photocuring the dental composition.

15. The method of claim 14, wherein the nitrogen-doped $TiO_2$ NPs further comprise one or more dopants selected from the group consisting of Ag (silver), F (fluorine), P (phosphorus), and $PO_4$ (phosphate).

16. The method of claim 14, wherein the polymer precursor is selected from the group consisting of acrylates, methacrylates, dimethacrylates, epoxies, vinyls and thiols.

17. The method of claim 14, wherein the polymer precursor is at least one selected from the group consisting of ethylenedimethacrylate (EDMA), bisphenol A glycidyl methacrylate (BisGMA), triethyleneglycol dimethacrylate (TEGDMA), 1,6-bis(methacryloxy-2-ethoxycarbonylamino)-2,4,4-trimethylhexane (UDMA), pyromellitic glycerol dimethacrylate (PMGDM), and 2-hydroxyethyl methacrylate (HEMA).

18. The method of claim 14, wherein the curable resin material is selected from the group consisting of dental resins, dental bonding agents, dental adhesives, dental cements, dental restoratives, dentals coatings, dental sealants, acrylic resins, and denture teeth.

19. The method of claim 14, wherein the dental composition comprises a volume to volume ratio of nitrogen-doped $TiO_2$ NPs to curable resin material in a range of 10% to 40% (v/v).

20. The method of claim 14, wherein the nitrogen-doped $TiO_2$ NPs have a N/Ti ratio of about 3.4.

* * * * *